US009469919B2

(12) United States Patent
Kuhn et al.

(10) Patent No.: US 9,469,919 B2
(45) Date of Patent: *Oct. 18, 2016

(54) METHOD OF ATTACHING A CELL-OF-INTEREST TO A MICROTUBE

(75) Inventors: Jonathan Charles Kuhn, Haifa (IL); Eyal Zussman, Haifa (IL); Michal Green, Haifa (IL); Shiri Klein, Tel-Aviv (IL)

(73) Assignee: TECHNION RESEARCH & DEVELOPMENT FOUNDATION LTD., Haifa (IL)

( * ) Notice: Subject to any disclaimer, the term of this patent is extended or adjusted under 35 U.S.C. 154(b) by 421 days.

This patent is subject to a terminal disclaimer.

(21) Appl. No.: 12/918,365

(22) PCT Filed: Feb. 12, 2009

(86) PCT No.: PCT/IL2009/000169
§ 371 (c)(1),
(2), (4) Date: Nov. 4, 2010

(87) PCT Pub. No.: WO2009/104174
PCT Pub. Date: Aug. 27, 2009

(65) Prior Publication Data
US 2011/0039296 A1    Feb. 17, 2011

Related U.S. Application Data

(60) Provisional application No. 61/064,210, filed on Feb. 21, 2008, provisional application No. 61/064,206, filed on Feb. 21, 2008, provisional application No. 61/064,204, filed on Feb. 21, 2008.

(51) Int. Cl.
*D01D 5/24*    (2006.01)
*D01F 1/08*    (2006.01)
(Continued)

(52) U.S. Cl.
CPC ............. *D01D 5/003* (2013.01); *A61K 9/0092* (2013.01); *B82Y 30/00* (2013.01); *C02F 3/102* (2013.01);
(Continued)

(58) Field of Classification Search
CPC ........ A61K 9/00; A61K 9/48; A61K 9/4816; A61K 9/50; A61K 9/5005; A61K 9/0092; D01D 5/003
See application file for complete search history.

(56) References Cited

U.S. PATENT DOCUMENTS 4,921,475 A    5/1990    Sibalis
5,209,734 A    5/1993    Hurley et al.
(Continued)

FOREIGN PATENT DOCUMENTS

AU    2007303821    4/2008
CN    1799649    7/2006
(Continued)

OTHER PUBLICATIONS

Kim et al. Controlled protein release from electrospun biodegradable fiber mesh composed of poly(E-caprolactone) and poly(ethylene oxide), International Journal of Pharmaceutics 2007, vol. 338, pp. 276-283.*
(Continued)

*Primary Examiner* — Shafiqul Haq
(74) *Attorney, Agent, or Firm* — The Roy Gross Law Firm, LLC; Roy Gross

(57) ABSTRACT

A method of attaching a cell or a membrane-coated particle-of-interest to a microtube is provided. The method comprising: co-electrospinning two polymeric solutions through co-axial capillaries, wherein a first polymeric solution of the two polymeric solutions is for forming a shell of the microtube and a second polymeric solution of the two polymeric solutions is for forming a coat over an internal surface of the shell, the first polymeric solution is selected solidifying faster than the second polymeric solution and a solvent of the second polymeric solution is selected incapable of dissolving the first polymeric solution and wherein the second polymeric solution comprises the cell or the membrane-coated particle-of-interest, thereby attaching the cell or the membrane-coated panicle-of-interest to the microtube. Also provided are microtubes with attached, entrapped or encapsulated cells or membrane-coated particles and methods of using same.

16 Claims, 5 Drawing Sheets
(1 of 5 Drawing Sheet(s) Filed in Color)

(51) Int. Cl.
*A61K 9/00* (2006.01)
*D01D 5/00* (2006.01)
*B82Y 30/00* (2011.01)
*C02F 3/10* (2006.01)
*C02F 3/34* (2006.01)
*D01D 5/247* (2006.01)
*D01F 1/10* (2006.01)
*D01F 8/14* (2006.01)
*G01N 33/543* (2006.01)
*C02F 101/18* (2006.01)
*C02F 101/20* (2006.01)
*C02F 101/30* (2006.01)
*C02F 101/36* (2006.01)

(52) U.S. Cl.
CPC ............... *C02F 3/34* (2013.01); *C02F 3/342* (2013.01); *D01D 5/247* (2013.01); *D01F 1/10* (2013.01); *D01F 8/14* (2013.01); *G01N 33/54393* (2013.01); *C02F 2101/18* (2013.01); *C02F 2101/20* (2013.01); *C02F 2101/306* (2013.01); *C02F 2101/36* (2013.01); *C02F 2305/08* (2013.01); *Y02W 10/15* (2015.05); *Y10T 428/1393* (2015.01)

(56) References Cited

U.S. PATENT DOCUMENTS

| | | | |
|---|---|---|---|
| 5,688,501 | A | 11/1997 | Merril et al. |
| 5,795,340 | A | 8/1998 | Lang |
| 6,537,195 | B2 | 3/2003 | Forman |
| 6,537,241 | B1 | 3/2003 | Odland |
| 7,066,922 | B2 | 6/2006 | Angel et al. |
| 2001/0014394 | A1 | 8/2001 | Soane et al. |
| 2001/0034503 | A1 | 10/2001 | Mehier |
| 2003/0098518 | A1* | 5/2003 | Averdung et al. ............. 264/10 |
| 2003/0135158 | A1 | 7/2003 | Gonnelli |
| 2003/0139727 | A1 | 7/2003 | Angel et al. |
| 2004/0018226 | A1 | 1/2004 | Wnek et al. |
| 2004/0030377 | A1 | 2/2004 | Dubson et al. |
| 2004/0147903 | A1 | 7/2004 | Latini |
| 2004/0223954 | A1 | 11/2004 | Bruessow et al. |
| 2005/0180992 | A1 | 8/2005 | Belcher et al. |
| 2006/0119015 | A1 | 6/2006 | Wehrspohn et al. |
| 2006/0200232 | A1 | 9/2006 | Phaneuf et al. |
| 2006/0226580 | A1 | 10/2006 | Xia et al. |
| 2006/0228435 | A1 | 10/2006 | Andrady et al. |
| 2009/0061496 | A1 | 3/2009 | Kuhn et al. |
| 2010/0129656 | A1* | 5/2010 | Zussman et al. ............. 428/376 |
| 2010/0303881 | A1 | 12/2010 | Hoke et al. |
| 2011/0081394 | A1* | 4/2011 | Zussman et al. ............. 424/422 |

FOREIGN PATENT DOCUMENTS

| | | |
|---|---|---|
| EP | 2079860 | 7/2009 |
| WO | WO 03/000381 | 1/2003 |
| WO | WO 2006/019293 | 2/2006 |
| WO | WO 2006019293 A1 * | 2/2006 |
| WO | WO 2006/108809 | 10/2006 |
| WO | WO 2008/041183 | 4/2008 |
| WO | WO 2009/104174 | 8/2009 |
| WO | WO 2009/104175 | 8/2009 |
| WO | WO 2009/104176 | 8/2009 |

OTHER PUBLICATIONS

Restriction Official Action Dated Dec. 23, 2011 From the US Patent and Trademark Office Re. U.S. Appl. No. 12/311,601.
Translation of Office Action Dated Dec. 4, 2012 From the State Intellectual Property Office of the People's Republic of China Re. Application No. 200780044536.1.
Official Action Dated Oct. 1, 2010 From the US Patent and Trademark Office Re. U.S. Appl. No. 11/896,130.
Lee et al. "Virus-Based Fabrication of Micro- and Nanofibers Using Electrospinning", NanoLetters, 4(3): 387-390, 2004.
Salalha et al. "Encapsulation of Bacteria and Viruses in Electrospun Nanofibres", Nanotechnology, 17: 4675-4681, Aug. 30, 2006.
Theron et al. "Electrostatic Field-Assisted Alignment of Electrospun Nanofibres", Nanotechnology, 12: 384-390, 2001.
Official Action Dated Feb. 7, 2013 From the US Patent and Trademark Office Re. U.S. Appl. No. 12/311,601.
Official Action Dated Feb. 14, 2012 From the US Patent and Trademark Office Re. U.S. Appl. No. 12/311,601.
Li et al. "Nano-Porous Ultra-High Specific Surface Ultrafine Fibers", Chinese Science Bulletin, 49(22): 2368-2371, Nov. 2004.
Communication Under Rule 71(3) EPC Dated Mar. 5, 2013 From the European Patent Office Re. Application No. 07826621.0.
Response Dated Feb. 1, 2011 to Official Action of Oct. 1, 2010 From the US Patent and Trademark Office Re. U.S. Appl. No. 11/896,130.
Official Action Dated Mar. 11, 2013 From the US Patent and Trademark Office Re. U.S. Appl. No. 12/918,372.
Kim et al. "Controlled Protein Release From Electrospun Biodegradable Fiber Mesh Composed of Poly(Epsilon-Caprolactone) and Poly(Ethylene Oxide)", International Journal of Pharmaceutics, 338: 276-283, 2007.
Zhang et al. "Biomimetic and Bioactive Nanofibrous Scaffolds From Electrospun Composite Nanofibers", International Journal of Nanomedicine, 2(4): 623-638, 2007.
Advisory Action Before the Filing of an Appeal Brief Dated Apr. 12, 2013 From the US Patent and Trademark Office Re. U.S. Appl. No. 12/311,601.
Official Action Dated Apr. 8, 2013 From the US Patent and Trademark Office Re. U.S. Appl. No. 12/918,377.
Response Dated Mar. 24, 2011 to Office Action of Oct. 13, 2010 From the State Intellectual Property Office of the People's Republic of China Re. Application No. 200780044536.1.
Official Action Dated Apr. 7, 2011 From the US Patent and Trademark Office Re. U.S. Appl. No. 11/896,130.
Zussman et al. "Formation of Nanofiber Crossbar in Electrospinning", Applied Physics Letters, 82(6): 973-975, Feb. 10, 2003.
Restriction Official Action Dated May 9, 2012 From the US Patent and Trademark Office Re. U.S. Appl. No. 12/918,372.
Advisory Action Before the Filing of An Appeal Brief Dated May 16, 2013 From the US Patent and Trademark Office Re. U.S. Appl. No. 12/311,601.
Official Action Dated Jun. 20, 2012 From the US Patent and Trademark Office Re. U.S. Appl. No. 12/918,377.
Communication Pursuant to Article 94(3) EPC Dated Jul. 18, 2012 From the European Patent Office Re. Application No. 09713280.7.
Communication Pursuant to Article 94(3) EPC Dated Jul. 19, 2012 From the European Patent Office Re. Application No. 09712148.7.
Communication Pursuant to Article 94(3) EPC Dated Jul. 19, 2012 From the European Patent Office Re. Application No. 09713264.1.
Response Dated Aug. 2, 2011 to Official Action of Apr. 7, 2011 From the US Patent and Trademark Office Re. U.S. Appl. No. 11/896,130.
Larsson et al. "Detection of Number and Viability of *E. Coli* and *A. Hydrophila* With FISH Technique", Techneau, D.3.5.3, p. 1-30, Apr. 30, 2008.
Official Action Dated Aug. 8, 2012 From the US Patent and Trademark Office Re. U.S. Appl. No. 12/918,372.
International Preliminary Report on Patentability Dated Apr. 16, 2009 From the International Bureau of WIPO Re.: Application No. PCT/IB2007/054001.
International Search Report and the Written Opinion Dated Sep. 29, 2009 From the International Searching Authority Re.: Application No. PCT/IL2009/000169.
International Search Report and the Written Opinion Dated Sep. 29, 2009 From the International Searching Authority Re.: Application No. PCT/IL2009/000171.
International Search Report and the Written Opinion Dated Sep. 30, 2009 From the International Searching Authority Re.: Application No. PCT/IL2009/000170.

(56) References Cited

OTHER PUBLICATIONS

International Search Report Dated Oct. 14, 2008 From the International Searching Authority Re.: Appliation No. PCT/IB2007/054001.
Written Opinion Dated Oct. 14, 2008 From the International Searching Authority Re.: Application No. PCT/IB2007/054001.
Bognitzki et al. "Polymer, Metal, and Hybrid Nano- and Mesotubes by Coating Degradable Polymer Template Fibers (TUFT Process)", Advanced Materials, 12(9): 637-640, 2000.
Caruso et al. "Titanium Dioxide Tubes From Sol-Gel Coating of Electrospun Polymer Fibers", Advanced Materials, 13: 1577-1579, Oct. 16, 2001.
Dror et al. "One-Step Production of Polymeric Microtubes by Co-Electrospinning", Small, XP002497054, 3(6): 1064-1073, Jun. 4, 2007.
Huang et al. "Encapsulating Drugs in Biodegradable Ultrafine Fibers Through Co-Axial Electrospinning", Journal of Biomedical Materials Research, Part A, 77A: 169-179, 169, 2006.
Jiang et al. "A Facile Technique to Prepare Biodegradable Coaxial Electrospun Nanofibers for Controlled Release of Bioactive Agents", Journal of Controlled Release, XP005163067, 108(2-3): 237-243, Nov. 28, 2005.
Jiang et al. "Modulation of Protein Release From Biodegradable Core-Shell Structured Fibers Prepared by Coaxial Electrospinning", Journal of Biomedical Materials Research Part B: Applied Biomaterials, 79B: 50-57, 2006.
Li et al. "Direct Fabrication of Composite and Ceramic Hollow Nanofibers by Electrospinning", Nano Letters, 4(5): 933-938, 2004.
Li et al. "Electrospinning of Nanofibers: Reinventing the Wheel?", Advanced Materials, 16(14): 1151-1170, Jul. 19, 2004.
Li et al. "Electrospinning: A Simple and Versatile Technique for Producing Ceramic Nanofibers and Nanotubes", Journal of the American Ceramic Society, 89(6): 1861-1869, 2006.
Li et al. "Use of Electrospinning to Directly Fabricate Hollow Nanofibers With Functionalized Inner and Outer Surfaces", Small, XP002497053, 1(1): 83-86, Jan. 1, 2005.
Loscertales et al. "Electrically Forced Coaxial Nanojets for One-Step Hollow Nanofiber Design", Journal of the American Chemical Society, JACS, 126: 5376-5377, 2004.
Loscertales et al. "Micro/Nano Encapsulation Via Electrified Coaxial Liquid Jets", Science, 295: 1695-1698, Mar. 16, 2002.
Reneker et al. "Electrospinning of Nanofibers From Polymer Solutions and Melts", Advances in Applied Mechanics, 41: 1-3, 103-115, 142-153, 2006.
Reznik et al. "Evolution of A Compound Droplet Attached to A Core-Shell Nozzle Under the Action of A Strong Electric Field", Physics of Fluids, 18: 062101-1-062101-13, 2006.
Salalha et al. "Encapsulation of Bacteria and Viruses in Electrospun Nanofibres", Nanotechnology, 17: 4675-4681, 2006.
Sun et al. "Compound Core-Shell Polymer Nanofibers by Co-Electrospinning", Advanced Materials, XP002497055, 15(22: 1929-1932, Nov. 17, 2003.
Xie et al. "Ultra-High Surface Fibrous Membranes From Electrospinning of Natural Proteins: Casein and Lipase Enzyme", Journal of Materials Science, 38: 2125-2133, 2003.
Yarin et al. "Material Encapsulation and Transport in Core-Shell Micro/Naonofibers, Polymer and Carbon Nanotubes and Micro/Nanochannels", Journal of Materials Chemistry, XP002546457, 17(25): 2585-2599, Jul. 1, 2007. Chapter III Section (ii).
Yu et al. "Production of Submicrometer Diameter Fibers by Two-Fluid Electrospinning", Advanced Materials, 16(17): 1562-1566, Sep. 3, 2004.
Zhang et al. "Coaxial Electrospinning of (Fluorescein Isothiocyanate-Conjugated Bovine Serum Albumin)-Encapsulated Poly(s-Caprolactone) Nanofibers for Sustained Release", Biomacromolecules, 7(4): 1049-1057, 2006.
Zussman et al. "Electrospun Polyacrylonitrile/Poly(Methyl Methacrylate)-Derived Turbostratic Carbon Micro-/Nanotubes", Advanced Materials, 18: 348-353, 2006.

International Preliminary Report on Patentability Dated Sep. 2, 2010 From the International Bureau of WIPO Re. Application No. PCT/IL2009/000171.
International Preliminary Report on Patentability Dated Sep. 2, 2010 From the International Bureau of WIPO Re.: Application No. PCT/IL2009/000169.
International Preliminary Report on Patentability Dated Sep. 2, 2010 From the International Bureau of WIPO Re.: Application No. PCT/IL2009/0001790.
Official Action Dated Aug. 27, 2012 From the US Patent and Trademark Office Re. U.S. Appl. No. 12/311,601.
Zhang et al. "Coaxial Electrospinning of (Fluorescein Isothiocyanate-Conjugated Bovine Serum Albumin)-Encapsulated Poly($\epsilon$-Caprolactone) Nanofibers for Sustained Release", Biomacromolecules, 7(4): 1049-1057, 2006.
Official Action Dated Nov. 3, 2011 From the US Patent and Trademark Office Re. U.S. Appl. No. 11/896,130.
Patent Examination Report Dated Nov. 19, 2012 From the Australian Government, IP Australia Re. Application No. 2007303821.
Communication Pursuant to Article 94(3) EPC Dated Dec. 2, 2011 From the European Patent Office Re. Application No. 07826621.0.
Translation of Office Action Dated Oct. 13, 2010 From the State Intellectual Property Office of the People's Republic of China Re. Application No. 200780044536.1.
He et al. "Recent Development of the Nanocomposites Prepared by Coaxial Jet Technology", Acta Materiae Compositae Sinica, 22(6): 1-8, Dec. 2005. Abstract in English.
Li et al. "Porous Ultrafine Nanofibers Having a Ultrahigh Specific Surface Area", Chinese Science Bulletin, 49(21): 2160-2163, Nov. 2004. Chinese Only!
Translation of Office Action Dated Jun. 4, 2013 From the State Intellectual Property Office of the People's Republic of China Re. Application No. 200780044536.1.
Decision to Grant a European Patent Pursuant to Article 97(1) EPC Dated Jul. 11, 2013 From the European Patent Office Re. Application No. 07826621.0.
Communication Under Rule 71(3) EPC Dated Dec. 10, 2013 From the European Patent Office Re. Application No. 09712148.7.
Office Action Dated Nov. 21, 2013 From the State Intellectual Property Office of the People's Republic of China Re. Application No. 200780044536.1 and Its Translation Into English.
Communication Pursuant to Article 94(3) EPC Dated Aug. 23, 2013 From the European Patent Office Re. Application No. 09713280.7.
Official Action Dated Sep. 6, 2013 From the US Patent and Trademark Office Re. U.S. Appl. No. 12/918,372.
Communication Pursuant to Article 94(3) EPC Dated Aug. 20, 2013 From the European Patent Office Re. Application No. 09713264.1.
Applicant-Initiated Interview Summary Dated Apr. 30, 2014 From the US Patent and Trademark Office Re. U.S. Appl. No. 12/918,372.
Requisition by the Examiner Dated May 22, 2014 From the Canadian Intellectual Property Office Re. Application No. 2,664,972.
Official Action Dated Oct. 1, 2014 From the US Patent and Trademark Office Re. U.S. Appl. No. 11/896,130.
Official Action Dated Jan. 9, 2015 From the US Patent and Trademark Office Re. U.S. Appl. No. 12/918,377.
Official Action Dated Jan. 14, 2015 From the US Patent and Trademark Office Re. U.S. Appl. No. 12/311,601.
McCann et al. "Electrospinning of Nanofibers With Core-Sheath, Hollow, or Porous Structures", Journal of Materials Chemistry, 15: 735-738, 2005.
Official Action Dated Feb. 5, 2015 From the US Patent and Trademark Office Re. U.S. Appl. No. 12/918,372.
Requisition by the Examiner and Examination Search Report Dated Jan. 23, 2015 From the Canadian Intellectual Property Office Re. Application No. 2,664,972.
Applicant-Initiated Interview Summary Dated Jul. 29, 2015 From the US Patent and Trademark Office Re. U.S. Appl. No. 12/918,372.
Translation of Office Action Dated Mar. 1, 2012 From the State Intellectual Property Office of the People's Republic of China Re. Application No. 200780044536.1.

* cited by examiner

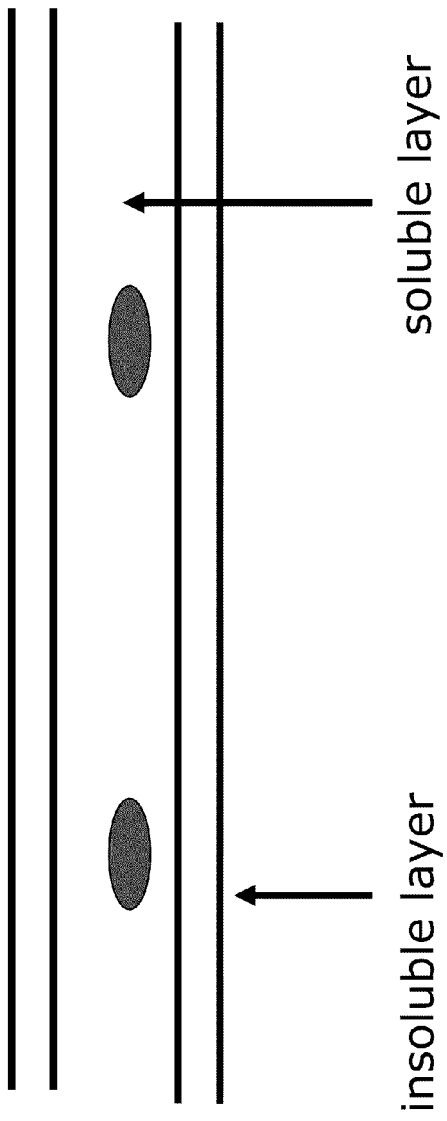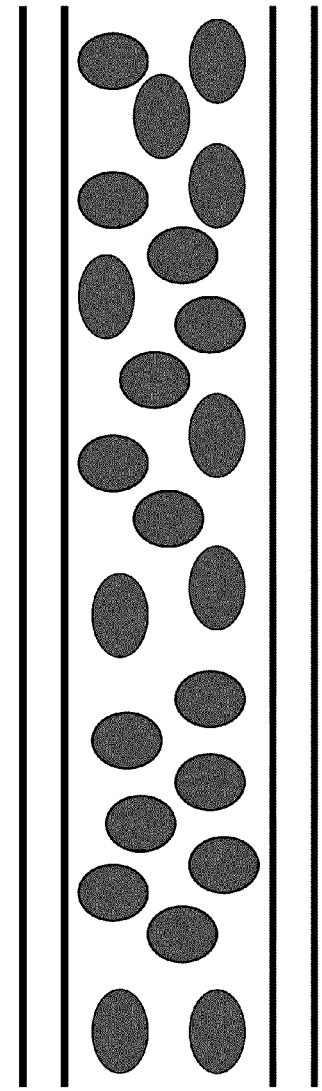
FIG. 3A
FIG. 3B

SEQUENCE LISTING

<160> NUMBER OF SEQ ID NOS: 7

<210> SEQ ID NO 1
<211> LENGTH: 474

<212> TYPE: PRT
<213> ORGANISM: Pseudomonas sp.

<400> SEQUENCE: 1

```
Met Gln Thr Leu Ser Ile Gln His Gly Thr Leu Val Thr Met Asp Gln
1               5                   10                  15

Tyr Arg Arg Val Leu Gly Asp Ser Trp Val His Val Gln Asp Gly Arg
            20                  25                  30

Ile Val Ala Leu Gly Val His Ala Glu Ser Val Pro Pro Pro Ala Asp
        35                  40                  45

Arg Val Ile Asp Ala Arg Gly Lys Val Val Leu Pro Gly Phe Ile Asn
    50                  55                  60

Ala His Thr His Val Asn Gln Ile Leu Leu Arg Gly Gly Pro Ser His
65                  70                  75                  80

Gly Arg Gln Phe Tyr Asp Trp Leu Phe Asn Val Val Tyr Pro Gly Gln
                85                  90                  95

Lys Ala Met Arg Pro Glu Asp Val Ala Val Ala Val Arg Leu Tyr Cys
            100                 105                 110

Ala Glu Ala Val Arg Ser Gly Ile Thr Thr Ile Asn Glu Asn Ala Asp
        115                 120                 125

Ser Ala Ile Tyr Pro Gly Asn Ile Glu Ala Ala Met Ala Val Tyr Gly
    130                 135                 140

Glu Val Gly Val Arg Val Val Tyr Ala Arg Met Phe Phe Asp Arg Met
145                 150                 155                 160

Asp Gly Arg Ile Gln Gly Tyr Val Asp Ala Leu Lys Ala Arg Ser Pro
                165                 170                 175

Gln Val Glu Leu Cys Ser Ile Met Glu Glu Thr Ala Val Ala Lys Asp
            180                 185                 190

Arg Ile Thr Ala Leu Ser Asp Gln Tyr His Gly Thr Ala Gly Gly Arg
        195                 200                 205

Ile Ser Val Trp Pro Ala Pro Ala Thr Thr Thr Ala Val Thr Val Glu
    210                 215                 220

Gly Met Arg Trp Ala Gln Ala Phe Ala Arg Asp Arg Ala Val Met Trp
225                 230                 235                 240

Thr Leu His Met Ala Glu Ser Asp His Asp Glu Arg Ile His Gly Met
                245                 250                 255

Ser Pro Ala Glu Tyr Met Glu Cys Tyr Gly Leu Leu Asp Glu Arg Leu
            260                 265                 270

Gln Val Ala His Cys Val Tyr Phe Asp Arg Lys Asp Val Arg Leu Leu
        275                 280                 285

His Arg His Asn Val Lys Val Ala Ser Gln Val Val Ser Asn Ala Tyr
    290                 295                 300

Leu Gly Ser Gly Val Ala Pro Val Pro Glu Met Val Glu Arg Gly Met
305                 310                 315                 320

Ala Val Gly Ile Gly Thr Asp Asn Gly Asn Ser Asn Asp Ser Val Asn
                325                 330                 335

Met Ile Gly Asp Met Lys Phe Met Ala His Ile His Arg Ala Val His
            340                 345                 350

Arg Asp Ala Asp Val Leu Thr Pro Glu Lys Ile Leu Glu Met Ala Thr
        355                 360                 365

Ile Asp Gly Ala Arg Ser Leu Gly Met Asp His Glu Ile Gly Ser Ile
    370                 375                 380

Glu Thr Gly Lys Arg Ala Asp Leu Ile Leu Leu Asp Leu Arg His Pro
385                 390                 395                 400
```

```
Gln Thr Thr Pro His His His Leu Ala Ala Thr Ile Val Phe Gln Ala
            405                 410                 415

Tyr Gly Asn Glu Val Asp Thr Val Leu Ile Asp Gly Asn Val Val Met
            420                 425                 430

Glu Asn Arg Arg Leu Ser Phe Leu Pro Pro Glu Arg Glu Leu Ala Phe
            435                 440                 445

Leu Glu Glu Ala Gln Ser Arg Ala Thr Ala Ile Leu Gln Arg Ala Asn
            450                 455                 460

Met Val Ala Asn Pro Ala Trp Arg Ser Leu
465                 470

<210> SEQ ID NO 2
<211> LENGTH: 481
<212> TYPE: PRT
<213> ORGANISM: Pseudomonas sp.

<400> SEQUENCE: 2

Met Thr Thr Thr Leu Tyr Thr Gly Phe His Gln Leu Val Thr Gly Asp
1               5                   10                  15

Val Ala Gly Thr Val Leu Asn Gly Val Asp Ile Leu Val Arg Asp Gly
            20                  25                  30

Glu Ile Ile Gly Leu Gly Pro Asp Leu Pro Arg Thr Leu Ala Pro Ile
            35                  40                  45

Gly Val Gly Gln Glu Gln Gly Val Glu Val Val Asn Cys Arg Gly Leu
        50                  55                  60

Thr Ala Tyr Pro Gly Leu Ile Asn Thr His His Phe Phe Gln Ala
65                  70                  75                  80

Phe Val Arg Asn Leu Ala Pro Leu Asp Trp Thr Gln Leu Asp Val Leu
            85                  90                  95

Ala Trp Leu Arg Lys Ile Tyr Pro Val Phe Ala Leu Val Asp Glu Asp
            100                 105                 110

Cys Ile Tyr His Ser Thr Val Val Ser Met Ala Glu Leu Ile Lys His
            115                 120                 125

Gly Cys Thr Thr Ala Phe Asp His Gln Tyr Asn Tyr Ser Arg Arg Gly
        130                 135                 140

Gly Pro Phe Leu Val Asp Arg Gln Phe Asp Ala Ala Asn Leu Leu Gly
145                 150                 155                 160

Leu Arg Phe His Ala Gly Arg Gly Cys Ile Thr Leu Pro Met Ala Glu
            165                 170                 175

Gly Ser Thr Ile Pro Asp Ala Met Arg Glu Ser Thr Thr Phe Leu
            180                 185                 190

Ala Asp Cys Glu Arg Leu Val Ser Arg Phe His Asp Pro Arg Pro Phe
            195                 200                 205

Ala Met Gln Arg Val Val Val Ala Pro Ser Ser Pro Val Ile Ala Tyr
        210                 215                 220

Pro Glu Thr Phe Val Glu Ser Ala Arg Leu Ala Arg His Leu Gly Val
225                 230                 235                 240

Ser Leu His Thr His Leu Gly Glu Gly Glu Thr Pro Ala Met Val Ala
            245                 250                 255

Arg Phe Gly Glu Arg Ser Leu Asp Trp Cys Glu Asn Arg Gly Phe Val
            260                 265                 270

Gly Pro Asp Val Trp Leu Ala His Gly Trp Glu Phe Thr Ala Ala Asp
        275                 280                 285

Ile Ala Arg Leu Ala Ala Thr Gly Thr Gly Val Ala His Cys Pro Ala
```

```
                290                 295                 300
Pro Val Phe Leu Val Gly Ala Glu Val Thr Asp Ile Pro Ala Met Ala
305                 310                 315                 320

Ala Ala Gly Val Arg Val Gly Phe Gly Val Asp Gly His Ala Ser Asn
                325                 330                 335

Asp Ser Ser Asn Leu Ala Glu Cys Ile Arg Leu Ala Tyr Leu Leu Gln
                340                 345                 350

Cys Leu Lys Ala Ser Glu Arg Gln His Pro Val Pro Ala Pro Tyr Asp
            355                 360                 365

Phe Leu Arg Met Ala Thr Gln Gly Gly Ala Asp Cys Leu Asn Arg Pro
        370                 375                 380

Asp Leu Gly Ala Leu Ala Val Gly Arg Ala Ala Asp Phe Phe Ala Val
385                 390                 395                 400

Asp Leu Asn Arg Ile Glu Tyr Ile Gly Ala Asn His Asp Pro Arg Ser
                405                 410                 415

Leu Pro Ala Lys Val Gly Phe Ser Gly Pro Val Asp Met Thr Val Ile
            420                 425                 430

Asn Gly Lys Val Val Trp Arg Asn Gly Glu Phe Pro Gly Leu Asp Glu
        435                 440                 445

Met Glu Leu Ala Arg Ala Ala Asp Gly Val Phe Arg Arg Val Ile Tyr
    450                 455                 460

Gly Asp Pro Leu Val Ala Ala Leu Arg Arg Gly Thr Gly Val Thr Pro
465                 470                 475                 480

Cys

<210> SEQ ID NO 3
<211> LENGTH: 403
<212> TYPE: PRT
<213> ORGANISM: Pseudomonas sp.

<400> SEQUENCE: 3

Met Ser Lys Asp Phe Asp Leu Ile Ile Arg Asn Ala Tyr Leu Ser Glu
1               5                   10                  15

Lys Asp Ser Val Tyr Asp Ile Gly Ile Val Gly Asp Arg Ile Ile Lys
            20                  25                  30

Ile Glu Ala Lys Ile Glu Gly Thr Val Lys Asp Glu Ile Asp Ala Lys
        35                  40                  45

Gly Asn Leu Val Ser Pro Gly Phe Val Asp Ala His Thr His Met Asp
    50                  55                  60

Lys Ser Phe Thr Ser Thr Gly Glu Arg Leu Pro Lys Phe Trp Ser Arg
65                  70                  75                  80

Pro Tyr Thr Arg Asp Ala Ala Ile Glu Asp Gly Leu Lys Tyr Tyr Lys
                85                  90                  95

Asn Ala Thr His Glu Glu Ile Lys Arg His Val Ile Glu His Ala His
            100                 105                 110

Met Gln Val Leu His Gly Thr Leu Tyr Thr Arg Thr His Val Asp Val
        115                 120                 125

Asp Ser Val Ala Lys Thr Lys Ala Val Glu Ala Val Leu Glu Ala Lys
    130                 135                 140

Glu Glu Leu Lys Asp Leu Asp Ile Gln Val Val Ala Phe Ala Gln
145                 150                 155                 160

Ser Gly Phe Phe Val Asp Leu Glu Ser Glu Ser Leu Ile Arg Lys Ser
                165                 170                 175

Leu Asp Met Gly Cys Asp Leu Val Gly Gly Val Asp Pro Ala Thr Arg
```

```
            180                 185                 190
Glu Asn Asn Val Glu Gly Ser Leu Asp Leu Cys Phe Lys Leu Ala Lys
        195                 200                 205

Glu Tyr Asp Val Asp Ile Asp Tyr His Ile His Asp Ile Gly Thr Val
    210                 215                 220

Gly Val Tyr Ser Ile Asn Arg Leu Ala Gln Lys Thr Ile Glu Asn Gly
225                 230                 235                 240

Tyr Lys Gly Arg Val Thr Thr Ser His Ala Trp Cys Phe Ala Asp Ala
            245                 250                 255

Pro Ser Glu Trp Leu Asp Glu Ala Ile Pro Leu Tyr Lys Asp Ser Gly
        260                 265                 270

Met Lys Phe Val Thr Cys Phe Ser Ser Thr Pro Thr Met Pro Val
    275                 280                 285

Ile Lys Leu Leu Glu Ala Gly Ile Asn Leu Gly Cys Ala Ser Asp Asn
        290                 295                 300

Ile Arg Asp Phe Trp Val Pro Phe Gly Asn Gly Asp Met Val Gln Gly
305                 310                 315                 320

Ala Leu Ile Glu Thr Gln Arg Leu Glu Leu Lys Thr Asn Arg Asp Leu
            325                 330                 335

Gly Leu Ile Trp Lys Met Ile Thr Ser Glu Gly Ala Arg Val Leu Gly
        340                 345                 350

Ile Glu Lys Asn Tyr Gly Ile Glu Val Gly Lys Ala Asp Leu Val
    355                 360                 365

Val Leu Asn Ser Leu Ser Pro Gln Trp Ala Ile Ile Asp Gln Ala Lys
370                 375                 380

Arg Leu Cys Val Ile Lys Asn Gly Arg Ile Ile Val Lys Asp Glu Val
385                 390                 395                 400

Ile Val Ala

<210> SEQ ID NO 4
<211> LENGTH: 363
<212> TYPE: PRT
<213> ORGANISM: Pseudomonas sp.

<400> SEQUENCE: 4

Met Tyr His Ile Asp Val Phe Arg Ile Pro Cys His Ser Pro Gly Asp
1               5                   10                  15

Thr Ser Gly Leu Glu Asp Leu Ile Glu Thr Gly Arg Val Ala Pro Ala
            20                  25                  30

Asp Ile Val Ala Val Met Gly Lys Thr Glu Gly Asn Gly Cys Val Asn
        35                  40                  45

Asp Tyr Thr Arg Glu Tyr Ala Thr Ala Met Leu Ala Ala Cys Leu Gly
    50                  55                  60

Arg His Leu Gln Leu Pro Pro His Glu Val Glu Lys Arg Val Ala Phe
65                  70                  75                  80

Val Met Ser Gly Gly Thr Glu Gly Val Leu Ser Pro His His Thr Val
                85                  90                  95

Phe Ala Arg Arg Pro Ala Ile Asp Ala His Arg Pro Ala Gly Lys Arg
            100                 105                 110

Leu Thr Leu Gly Ile Ala Phe Thr Arg Asp Phe Leu Pro Glu Glu Ile
        115                 120                 125

Gly Arg His Ala Gln Ile Thr Glu Thr Ala Gly Ala Val Lys Arg Ala
    130                 135                 140

Met Arg Asp Ala Gly Ile Ala Ser Ile Asp Asp Leu His Phe Val Gln
```

```
                145                 150                 155                 160
        Val Lys Cys Pro Leu Leu Thr Pro Ala Lys Ile Ala Ser Ala Arg Ser
                        165                 170                 175

Arg Gly Cys Ala Pro Val Thr Thr Asp Thr Tyr Glu Ser Met Gly Tyr
                        180                 185                 190

Ser Arg Gly Ala Ser Ala Leu Gly Ile Ala Leu Ala Thr Glu Glu Val
                        195                 200                 205

Pro Ser Ser Met Leu Val Asp Glu Ser Val Leu Asn Asp Trp Ser Leu
                210                 215                 220

Ser Ser Ser Leu Ala Ser Ala Ser Ala Gly Ile Glu Leu Glu His Asn
        225                 230                 235                 240

Val Val Ile Ala Ile Gly Met Ser Glu Gln Ala Thr Ser Glu Leu Val
                        245                 250                 255

Ile Ala His Gly Val Met Ser Asp Ala Ile Asp Ala Ala Ser Val Arg
                        260                 265                 270

Arg Thr Ile Glu Ser Leu Gly Ile Arg Ser Asp Asp Glu Met Asp Arg
                        275                 280                 285

Ile Val Asn Val Phe Ala Lys Ala Glu Ala Ser Pro Asp Gly Val Val
                290                 295                 300

Arg Gly Met Arg His Thr Met Leu Ser Asp Ser Asp Ile Asn Ser Thr
        305                 310                 315                 320

Arg His Ala Arg Ala Val Thr Gly Ala Ala Ile Ala Ser Val Val Gly
                        325                 330                 335

His Gly Met Val Tyr Val Ser Gly Gly Ala Glu His Gln Gly Pro Ala
                        340                 345                 350

Gly Gly Gly Pro Phe Ala Val Ile Ala Arg Ala
                        355                 360

<210> SEQ ID NO 5
<211> LENGTH: 457
<212> TYPE: PRT
<213> ORGANISM: Pseudomonas sp.

<400> SEQUENCE: 5

Met Lys Thr Val Glu Ile Ile Glu Gly Ile Ala Ser Gly Arg Thr Ser
        1               5                   10                  15

Ala Arg Asp Val Cys Glu Glu Ala Leu Ala Thr Ile Gly Ala Thr Asp
                        20                  25                  30

Gly Leu Ile Asn Ala Phe Thr Cys Arg Thr Val Glu Arg Ala Arg Ala
                        35                  40                  45

Glu Ala Asp Ala Ile Asp Val Arg Arg Ala Arg Gly Glu Val Leu Pro
                50                  55                  60

Pro Leu Ala Gly Leu Pro Tyr Ala Val Lys Asn Leu Phe Asp Ile Glu
        65                  70                  75                  80

Gly Val Thr Thr Leu Ala Gly Ser Lys Ile Asn Arg Thr Leu Pro Pro
                        85                  90                  95

Ala Arg Ala Asp Ala Val Leu Val Gln Arg Leu Lys Ala Ala Gly Ala
                        100                 105                 110

Val Leu Leu Gly Gly Leu Asn Met Asp Glu Phe Ala Tyr Gly Phe Thr
                        115                 120                 125

Thr Glu Asn Thr His Tyr Gly Pro Thr Arg Asn Pro His Asp Thr Gly
                130                 135                 140

Arg Ile Ala Gly Gly Ser Ser Gly Gly Ser Ala Ala Ile Ala Ala
        145                 150                 155                 160
```

-continued

Gly Gln Val Pro Leu Ser Leu Gly Ser Asp Thr Asn Gly Ser Ile Arg
            165                 170                 175

Val Pro Ala Ser Leu Cys Gly Val Trp Gly Leu Lys Pro Thr Phe Gly
        180                 185                 190

Arg Leu Ser Arg Arg Gly Thr Tyr Pro Phe Val His Ser Ile Asp His
    195                 200                 205

Leu Gly Pro Leu Ala Asp Ser Val Glu Gly Leu Ala Leu Ala Tyr Asp
210                 215                 220

Ala Met Gln Gly Pro Asp Pro Leu Asp Pro Gly Cys Ser Ala Ser Arg
225                 230                 235                 240

Ile Gln Pro Ser Val Pro Val Leu Ser Gln Gly Ile Ala Gly Leu Arg
            245                 250                 255

Ile Gly Val Leu Gly Gly Trp Phe Arg Asp Asn Ala Gly Pro Ala Ala
        260                 265                 270

Arg Ala Ala Val Asp Val Ala Ala Leu Thr Leu Gly Ala Ser Glu Val
    275                 280                 285

Val Met Trp Pro Asp Ala Glu Ile Gly Arg Ala Ala Phe Val Ile
290                 295                 300

Thr Ala Ser Glu Gly Gly Cys Leu His Leu Asp Asp Leu Arg Ile Arg
305                 310                 315                 320

Pro Gln Asp Phe Glu Pro Leu Ser Val Asp Arg Phe Ile Ser Gly Val
            325                 330                 335

Leu Gln Pro Val Ala Trp Tyr Leu Arg Ala Gln Arg Phe Arg Arg Val
        340                 345                 350

Tyr Arg Asp Lys Val Asn Ala Leu Phe Arg Asp Trp Asp Ile Leu Ile
    355                 360                 365

Ala Pro Ala Thr Pro Ile Ser Ala Pro Ala Ile Gly Thr Glu Trp Ile
370                 375                 380

Glu Val Asn Gly Thr Arg His Pro Cys Arg Pro Ala Met Gly Leu Leu
385                 390                 395                 400

Thr Gln Pro Val Ser Phe Ala Gly Cys Pro Val Val Ala Ala Pro Thr
            405                 410                 415

Trp Pro Gly Glu Asn Asp Gly Met Pro Ile Gly Val Gln Leu Ile Ala
        420                 425                 430

Ala Pro Trp Asn Glu Ser Leu Cys Leu Arg Ala Gly Lys Val Leu Gln
    435                 440                 445

Asp Thr Gly Ile Ala Arg Leu Lys Cys
    450                 455

<210> SEQ ID NO 6
<211> LENGTH: 605
<212> TYPE: PRT
<213> ORGANISM: Pseudomonas sp.

<400> SEQUENCE: 6

Met Asn Asp Arg Ala Pro His Pro Glu Arg Ser Gly Arg Val Thr Pro
1               5                   10                  15

Asp His Leu Thr Asp Leu Ala Ser Tyr Gln Ala Ala Tyr Ala Ala Gly
            20                  25                  30

Thr Asp Ala Ala Asp Val Ile Ser Asp Leu Tyr Ala Arg Ile Lys Glu
        35                  40                  45

Asp Gly Glu Asn Pro Ile Trp Ile Ser Leu Pro Leu Glu Ser Ala
    50                  55                  60

Leu Ala Met Leu Ala Asp Ala Gln Gln Arg Lys Asp Lys Gly Glu Ala
65                  70                  75                  80

```
Leu Pro Leu Phe Gly Ile Pro Phe Gly Val Lys Asp Asn Ile Asp Val
                85                  90                  95

Ala Gly Leu Pro Thr Thr Ala Gly Cys Thr Gly Phe Ala Arg Thr Pro
            100                 105                 110

Arg Gln His Ala Phe Val Val Gln Arg Leu Val Asp Ala Gly Ala Ile
        115                 120                 125

Pro Ile Gly Lys Thr Asn Leu Asp Gln Phe Ala Thr Gly Leu Asn Gly
    130                 135                 140

Thr Arg Thr Pro Phe Gly Ile Pro Arg Cys Val Phe Asn Glu Asn Tyr
145                 150                 155                 160

Val Ser Gly Gly Ser Ser Gly Ser Ala Val Ala Val Ala Asn Gly
                165                 170                 175

Thr Val Pro Phe Ser Leu Gly Thr Asp Thr Ala Gly Ser Gly Arg Ile
            180                 185                 190

Pro Ala Ala Phe Asn Asn Leu Val Gly Leu Lys Pro Thr Lys Gly Leu
        195                 200                 205

Phe Ser Gly Ser Gly Leu Val Pro Ala Ala Arg Ser Leu Asp Cys Ile
    210                 215                 220

Ser Val Leu Ala His Thr Val Asp Asp Ala Leu Ala Val Ala Arg Val
225                 230                 235                 240

Ala Ala Gly Tyr Asp Ala Asp Asp Ala Phe Ser Arg Lys Ala Gly Ala
                245                 250                 255

Ala Ala Leu Thr Glu Lys Ser Trp Pro Arg Arg Phe Asn Phe Gly Val
            260                 265                 270

Pro Ala Ala Glu His Arg Gln Phe Phe Gly Asp Ala Glu Ala Glu Ala
        275                 280                 285

Leu Phe Asn Lys Ala Val Arg Lys Leu Glu Glu Met Gly Gly Thr Cys
    290                 295                 300

Ile Ser Phe Asp Tyr Thr Pro Phe Arg Gln Ala Ala Glu Leu Leu Tyr
305                 310                 315                 320

Ala Gly Pro Trp Val Ala Glu Arg Leu Ala Ala Ile Glu Ser Leu Ala
                325                 330                 335

Asp Glu His Pro Glu Val Leu His Pro Val Val Arg Asp Ile Ile Leu
        340                 345                 350

Ser Ala Lys Arg Met Ser Ala Val Asp Thr Phe Asn Gly Ile Tyr Arg
    355                 360                 365

Leu Ala Asp Leu Val Arg Ala Ala Glu Ser Thr Trp Glu Lys Ile Asp
370                 375                 380

Val Met Leu Leu Pro Thr Ala Pro Thr Ile Tyr Thr Val Glu Asp Met
385                 390                 395                 400

Leu Ala Asp Pro Val Arg Leu Asn Ser Asn Leu Gly Phe Tyr Thr Asn
                405                 410                 415

Phe Val Asn Leu Met Asp Leu Ser Ala Ile Ala Val Pro Ala Gly Phe
        420                 425                 430

Arg Thr Asn Gly Leu Pro Phe Gly Val Thr Phe Ile Gly Arg Ala Phe
    435                 440                 445

Glu Asp Gly Ala Ile Ala Ser Leu Gly Lys Ala Phe Val Glu His Asp
450                 455                 460

Leu Ala Lys Gly Asn Ala Ala Thr Ala Ala Pro Pro Lys Asp Thr Val
465                 470                 475                 480

Ala Ile Ala Val Val Gly Ala His Leu Ser Asp Gln Pro Leu Asn His
                485                 490                 495
```

```
Gln Leu Thr Glu Ser Gly Gly Lys Leu Arg Ala Thr Thr Arg Thr Ala
            500                 505                 510
Pro Gly Tyr Ala Leu Tyr Ala Leu Arg Asp Ala Thr Pro Ala Lys Pro
        515                 520                 525
Gly Met Leu Arg Asp Gln Asn Ala Val Gly Ser Ile Glu Val Glu Ile
    530                 535                 540
Trp Asp Leu Pro Val Ala Gly Phe Gly Ala Phe Val Ser Glu Ile Pro
545                 550                 555                 560
Ala Pro Leu Gly Ile Gly Thr Ile Thr Leu Glu Asp Gly Ser His Val
            565                 570                 575
Lys Gly Phe Leu Cys Glu Pro His Ala Ile Glu Thr Ala Leu Asp Ile
        580                 585                 590
Thr His Tyr Gly Gly Trp Arg Ala Tyr Leu Ala Ala Gln
    595                 600                 605
```

<210> SEQ ID NO 7
<211> LENGTH: 225
<212> TYPE: PRT
<213> ORGANISM: Discosoma sp.

<400> SEQUENCE: 7

```
Met Arg Ser Ser Lys Asn Val Ile Lys Glu Phe Met Arg Phe Lys Val
1               5                   10                  15
Arg Met Glu Gly Thr Val Asn Gly His Glu Phe Glu Ile Glu Gly Glu
            20                  25                  30
Gly Glu Gly Arg Pro Tyr Glu Gly His Asn Thr Val Lys Leu Lys Val
        35                  40                  45
Thr Lys Gly Gly Pro Leu Pro Phe Ala Trp Asp Ile Leu Ser Pro Gln
    50                  55                  60
Phe Gln Tyr Gly Ser Lys Val Tyr Val Lys His Pro Ala Asp Ile Pro
65                  70                  75                  80
Asp Tyr Lys Lys Leu Ser Phe Pro Glu Gly Phe Lys Trp Glu Arg Val
            85                  90                  95
Met Asn Phe Glu Asp Gly Gly Val Val Thr Val Thr Gln Asp Ser Ser
        100                 105                 110
Leu Gln Asp Gly Cys Phe Ile Tyr Lys Val Lys Phe Ile Gly Val Asn
    115                 120                 125
Phe Pro Ser Asp Gly Pro Val Met Gln Lys Lys Thr Met Gly Trp Glu
130                 135                 140
Ala Ser Thr Glu Arg Leu Tyr Pro Arg Asp Gly Val Leu Lys Gly Glu
145                 150                 155                 160
Ile His Lys Ala Leu Lys Leu Lys Asp Gly Gly His Tyr Leu Val Glu
            165                 170                 175
Phe Lys Ser Ile Tyr Met Ala Lys Lys Pro Val Gln Leu Pro Gly Tyr
        180                 185                 190
Tyr Tyr Val Asp Ser Lys Leu Asp Ile Thr Ser His Asn Glu Asp Tyr
    195                 200                 205
Thr Ile Val Glu Gln Tyr Glu Arg Thr Glu Gly Arg His His Leu Phe
210                 215                 220
Leu
225
```

METHOD OF ATTACHING A CELL-OF-INTEREST TO A MICROTUBE

RELATED APPLICATIONS

This Application is a National Phase of PCT Patent Application No. PCT/IL2009/000169 having International filing date of Feb. 12, 2009, which claims the benefit of U.S. Provisional Patent Application Nos. 61/064,210, 61/064,206 and 61/064,204 filed on Feb. 21, 2008. The contents of the above Applications are all incorporated herein by reference.

The teachings of PCT/IB2007/054001 are incorporated herein by reference.

The contents of all of the above documents are incorporated by reference as if fully set forth herein.

FIELD AND BACKGROUND OF THE INVENTION

The present invention, in some embodiments thereof, relates to a method of attaching a cell or a membrane-coated particle-of-interest to a microtube and, more particularly, but not exclusively, to electrospun microtubes which include cells or membrane-coated particles attached, entrapped or encapsulated therein which can be used in various applications such as water purification, detoxification, mineral enrichment, tissue grafts and cell-based therapy.

Water purification usually entails the removal of toxic chemicals such as mercury, mercurial compounds, and cadmium or elements such as toluene, chloroform, benzene, pesticides and herbicides. Interestingly, although these organic compounds are not found in nature and result from modern industry and motor vehicles, certain bacterial strains have evolved mechanisms for degrading them while utilizing their carbon and nitrogen atoms.

For example, Pseudomonads can be used to degrade toluene (Moat and Foster, 1995), benzene, phenol, naphthalene (Doelle, 1969) and certain hydrocarbons from oil (van der Linden et al., 1965). In addition, atrazine, a commonly used toxic herbicide that enters the water supply, can be detoxified to ammonia and carbon di-oxide via a dechlorinization reaction mediated by *Pseudomonas* ADP. Thus, bioparticles of *Pseudomonas* ADP grown on granulated active carbon were shown capable of degrading atrazine in water (Herzberg et al., 2006). However, since the granulated active carbon particles are only effective for a limited time, a carbon source (citrate) must be added to the water as it enters the purification column, which may be associated with the growth of other bacterial species and increases the costs of the purification process.

Another serious problem which occurs in some water systems is the presence of toxic heavy metals such as cadmium and mercury. Several bacterial strains such as *Chromobacterium violaceum*, *Pseudomonas maltophila*, *Pseudomonas aeruginosa*, *Spirulina planensis*, *Staphylococcus aureus*, *Bacillus cereus*, *Bacillus subtilis* and *Escherichia coli* have been found capable of removing metal contamination, destroying the toxic complex containing the metallic ions (e.g., cadmium and tellurium) or recovering valuable metals such as platinum and palladium, gold and silver from the water. For example, certain bacteria have been used to form nanoparticles of valuable metals (Brayner et al., 2007).

Nanofibers and polymeric nanofibers in particular can be produced by the electrospinning process (Reneker D H., et al., 2006; Ramakrishna S., et al., 2005; Li D, et al., 2004; PCT WO 2006/106506 to Zussman, E., et al.). Sun and co-workers (Sun Z, et al., 2003) describe the production of core-shell nanofibers (i.e., filled fibers) by co-electrospinning of two polymeric solutions using a spinneret with two co-axial capillaries. US patent application No. 20060119015 to Wehrspohn R., et al. describes the production of hollow fibers by introducing a liquid containing a polymer to a porous template material, and removal of the template following polymer solidification. PCT/IB2007/054001 to Zussman, E., et al. (which is fully incorporated herein by reference) discloses methods of producing electrospun microtubes (i.e., hollow fibers) which can be further filled with liquids and be used as microfluidics.

Salalha W., et al., 2006, describe the encapsulation of whole bacterial cells and complex bacterial viruses in electrospun single-layer fibers, in which the entrapped cells or viruses retained both physiological activity and some of their viability, even after storing the dry electrospun mats for a number of months.

SUMMARY OF THE INVENTION

According to an aspect of some embodiments of the present invention there is provided a method of attaching a cell or a membrane-coated particle-of-interest to a microtube, the method comprising: co-electrospinning two polymeric solutions through co-axial capillaries, wherein a first polymeric solution of the two polymeric solutions is for forming a shell of the microtube and a second polymeric solution of the two polymeric solutions is for forming a coat over an internal surface of the shell, the first polymeric solution is selected solidifying faster than the second polymeric solution and a solvent of the second polymeric solution is selected incapable of dissolving the first polymeric solution and wherein the second polymeric solution comprises the cell or the membrane-coated particle-of-interest, thereby attaching the cell or the membrane-coated particle-of-interest to the microtube.

According to an aspect of some embodiments of the present invention there is provided a microtube comprising an electrospun shell, an electrospun coat over an internal surface of the shell and a cell or a membrane-coated particle-of-interest attached to the microtube.

According to an aspect of some embodiments of the present invention there is provided a method of bioremediation, the method comprising contacting a solution containing a contaminant with the microtube of some embodiments of the invention, wherein the cell, a portion of the cell or the membrane-coated particle-of-interest is capable of degrading or assimilating the contaminant.

According to an aspect of some embodiments of the present invention there is provided a method of depleting a molecule from a solution, comprising contacting the solution with the microtube of some embodiments of the invention, wherein the molecule is capable of binding to or being processed by the cell or the membrane-coated particle-of-interest, thereby depleting the molecule from the solution.

According to an aspect of some embodiments of the present invention there is provided a method of isolating a molecule from a solution, comprising: (a) contacting the solution with the microtube of some embodiments of the invention under conditions which allow binding of the molecule to the cell or the membrane-coated particle-of-interest, and; (b) eluting the molecule from the microtube; thereby isolating the molecule from the solution.

According to an aspect of some embodiments of the present invention there is provided a method of detecting a presence of a molecule in a sample, comprising: (a) contacting the sample with the microtube of some embodiments of the invention, wherein the cell or the membrane-coated particle-of-interest is capable of binding to or processing the molecule, and; (b) detecting the binding or the processing; thereby detecting the presence of the molecule in the sample.

According to some embodiments of the invention, the electrospun shell is formed of a first polymeric solution and the electrospun coat is formed of a second polymeric solution.

According to some embodiments of the invention, the first polymeric solution solidifies faster than the second polymeric solution.

According to some embodiments of the invention, a solvent of the second polymeric solution is incapable of dissolving the first polymeric solution.

According to some embodiments of the invention, the electrospun shell comprises a polymer selected from the group consisting of poly(e-caprolactone) (PCL), polyamide, poly(siloxane), poly(silicone), poly(ethylene), poly(vinyl pyrrolidone), poly(2-hydroxy ethylmethacrylate), poly(N-vinyl pyrrolidone), poly(methyl methacrylate), poly(vinyl alcohol), poly(acrylic acid), poly(vinyl acetate), polyacrylamide, poly(ethylene-co-vinyl acetate), poly(ethylene glycol), poly(methacrylic acid), polylactide, polyglycolide, poly(lactide-coglycolide), polyanhydride, polyorthoester, poly(carbonate), poly(acrylo nitrile), poly(ethylene oxide), polyaniline, polyvinyl carbazole, polystyrene, poly(vinyl phenol), polyhydroxyacid, poly(caprolactone), polyanhydride, polyhydroxyalkanoate, polyurethane, collagen, albumin, alginate, chitosan, starch and hyaluronic acid, and whereas the electrospun coat comprises a polymer selected from the group consisting of poly(acrylic acid), poly(vinyl acetate), polyacrylamide, poly(ethylene-co-vinyl acetate), poly(ethylene glycol), poly(methacrylic acid), polylactide polyglycolide, poly(lactide-coglycolide), polyanhydride, polyorthoester, poly(carbonate), poly(ethylene oxide), polyaniline, polyvinyl carbazole, polystyrene, poly(vinyl phenol), polyhydroxyacid, alginate, starch and hyaluronic acid.

According to some embodiments of the invention, a solvent of the first polymeric solution evaporates faster than a solvent of the second polymeric solution.

According to some embodiments of the invention, the electrospinning is effected using a rotating collector.

According to some embodiments of the invention, the solvent of the second polymeric solution is capable of evaporating through the internal surface of the shell.

According to some embodiments of the invention, the second polymeric solution is capable of wetting the internal surface of the shell.

According to some embodiments of the invention, a thickness of the shell is from about 100 nm to about 20 micrometer.

According to some embodiments of the invention, an internal diameter of the microtube is from about 50 nm to about 20 micrometer.

According to some embodiments of the invention, the first and the second polymeric solutions are selected from the group consisting of: 10% poly(e-caprolactone) (PCL) in chloroform ($CHCl_3$) and dimethylforamide (DMF) (80:20 by weight) as the first polymeric solution and 4% poly(ethylene oxide) (PEO) in water ($H_2O$) and ethanol (60:40 by weight) as the second polymeric solution, 10% PCL in $CHCl_3$ and DMF (80:20 by weight) as the first polymeric solution and 6% PEO in $H_2O$ and ethanol (60:40 by weight) as the second polymeric solution, 9% PCL in $CHCl_3$ and DMF (90:10 by weight) as the first polymeric solution and 7% PEO in $H_2O$ as the second polymeric solution, 10% PCL in $CHCl_3$ and DMF (80:20 by weight) as the first polymeric solution and 9% poly(vinyl alcohol) (PVA) in water and ethanol (50:50 by weight) as the second polymeric solution, and 10% PCL in $CHCl_3$ and DMF (90:10 by weight) as the first polymeric solution and 4% (w/w) PEO in ethanol:$H_2O$ (26:74 by weight) as a second polymeric solution.

According to some embodiments of the invention, the microtube is filled with a liquid.

According to some embodiments of the invention, the first and the second polymeric solutions are biocompatible.

According to some embodiments of the invention, the cell or the membrane-coated particle-of-interest is attached to the coat over the internal surface of the shell.

According to some embodiments of the invention, the cell or the membrane-coated particle-of-interest is attached to the shell of the microtube.

According to some embodiments of the invention, the first polymeric solution comprises polyethylene glycol (PEG).

According to some embodiments of the invention, the shell comprises pores.

According to some embodiments of the invention, the shell prevents diffusion of the cell or the membrane-coated particle-of-interest therethrough.

According to some embodiments of the invention, the cell comprises a prokaryotic cell.

According to some embodiments of the invention, the cell comprises a cell wall.

According to some embodiments of the invention, the contaminant comprises atrazine.

According to some embodiments of the invention, the method further comprising collecting said solution following the contacting.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1B:
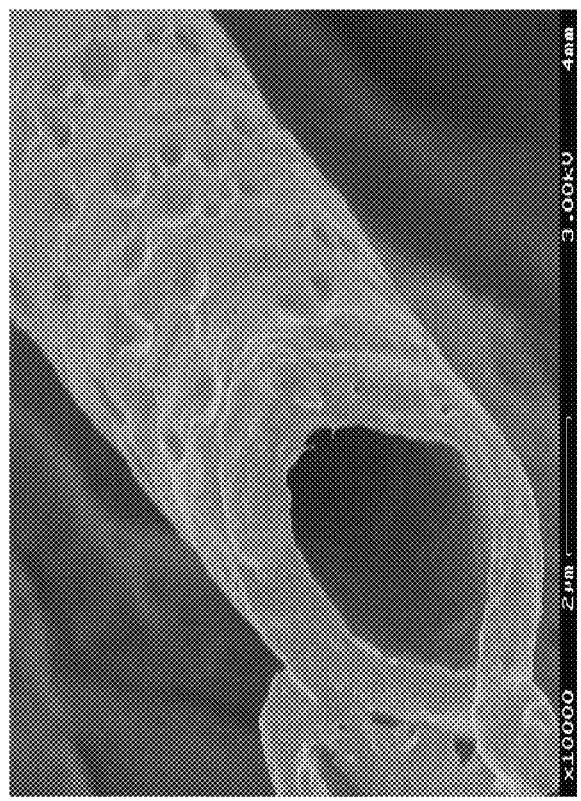
Figure 1A:
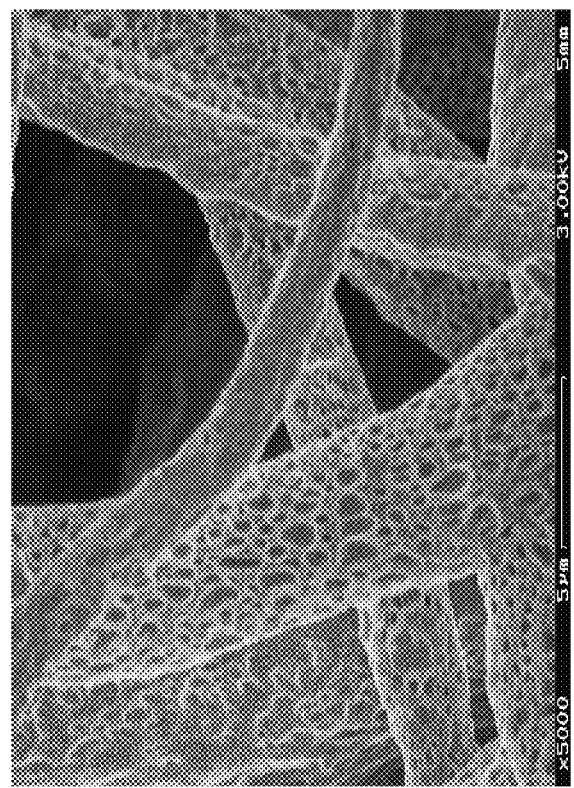

FIGS. 1A-B are images depicting high resolution scanning electron microscope (HRSEM) micrographs of the microtubes according to an embodiment of the invention which are attached to cells of microorganisms such that the cells are entrapped therein. Electrospinning was performed using a first polymeric solution (for forming the shell) which consisted of 9% [weight/weight (w/w)] polycaprolactone (PCL) dissolved in chloroform/DMSO [9:1 (w/w)]; and a second polymeric solution (for forming the coat over the internal surface of the shell) which consisted of 8% poly(ethylene oxide) (PEO) in water (w/w). FIG. 1A—Magnification of 5000×; FIG. 1B—Magnification of 10,000×.

Figure 2:
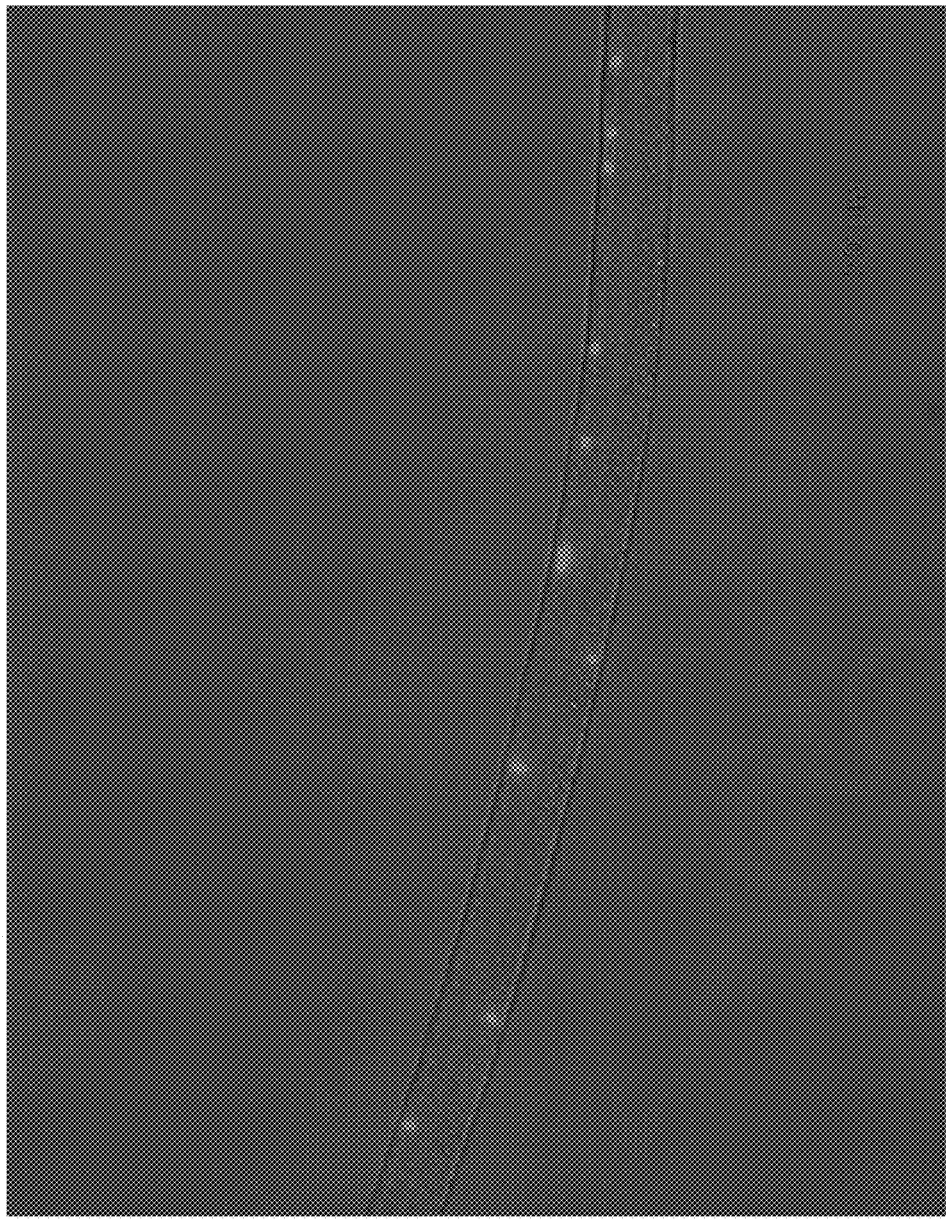

FIG. 2 is a microscopic image of Pseudomonas putida bacterial cells transformed with the DsRed expression vector encoding the red fluorescent protein [GenBank Accession No. Q9U6Y8 (SEQ ID NO:7)] and entrapped within a microtube of an embodiment of the invention. A microtube was formed by co-electrospinning of the two polymeric solutions: 9% (w/w) polycaprolactone (PCL) dissolved in chloroform/DMSO [9:1 (w/w)] as a first polymeric solution (for forming the shell); and 8% poly(ethylene oxide) (PEO) in water (w/w) as second polymeric solution (for forming the coat over the internal surface of the shell) which also included 100 μl of Pseudomonas putida bacterial cells (at a concentration of $10^9$ cells/ml). Detection of the bacterial cells within the microtube was performed using a fluorescence microscope. Red fluorescence of the red fluorescent protein (RFP) encoded by the DsRed expression vector was visualized at a wavelength of 359 nm for excitation and examining emitted light at a wavelength of 361 nm. Magnification: 200×; Size bar: 20 μm.

FIGS. 3A-B are schematic illustrations depicting the encapsulation of bacteria (FIG. 3A) and the growth of entrapped bacteria (FIG. 3B) within the microtube of some embodiments of the invention. FIG. 3A—A microtube is formed from two polymeric solutions, the first one, for forming the shell is insoluble in water, and the second one, for forming the coat over the internal surface of the shell is soluble in water (see for example, the description of solutions with FIG. 2, hereinabove). Following microtube formation, the microtube can be filled with an aqueous solution (e.g., water or phosphate buffer) by simply exposing the microtube to an aqueous solution (e.g., by immersing the microtube in the aqueous solution). The aqueous solution dissolves some of the polymer of the inner layer (the coat over the internal surface of the shell) which is mixed with the bacterial cells and the bacteria are released to the internal volume of the microtube. The bacteria (red circles) reside within the soluble layer. FIG. 3B—The bacteria (red circles) can proliferate within the soluble layer of the microtube when supplied with appropriate nutrients.

Figure 4:
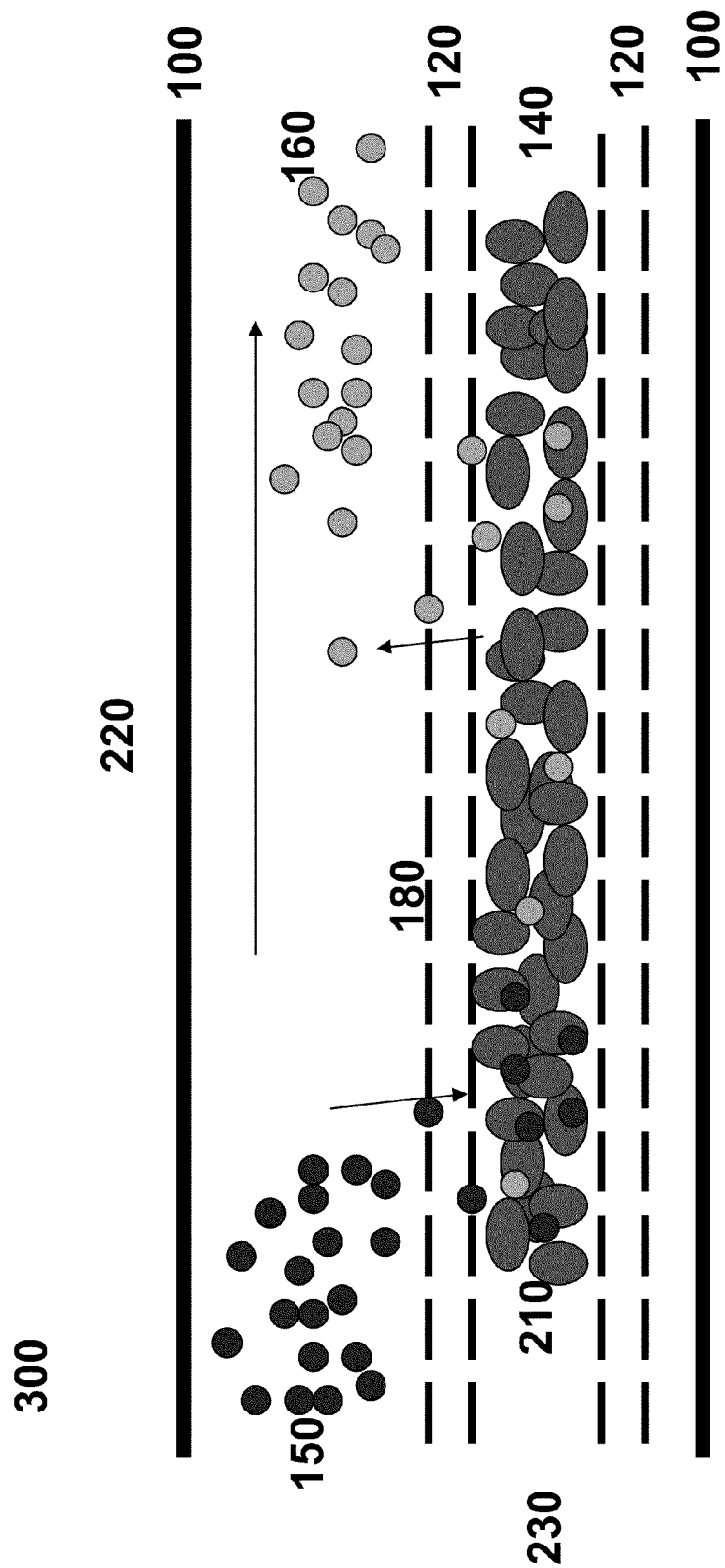

FIG. 4 is a schematic illustration of a bioremediation system generated according to some embodiments of the invention. System 300 comprises conduit [220, e.g., part of an aqueous system, can be a plastic or metal (e.g., copper) pipe/tube] having borders (100) includes microtube (230) with shell borders (120) and entrapped bacterial cells (210, red). For purification (e.g., detoxification of water), a liquid (e.g., drinking water) containing molecule (150, blue) flows within the conduit. Pores (180) within the microtube shell enable the diffusion of molecule (150) through the microtube shell to the microtube lumen (140) containing bacterial cells (210). Cells (210) interact with molecule (150) and reaction product (160, green) diffuses out of the microtube outside of the microtube lumen (140) through the microtube shell pores (180).

Figure 5:
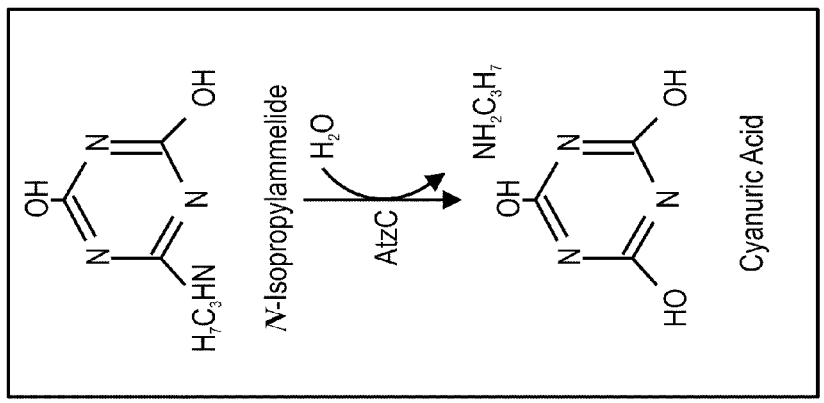
Figure 5:
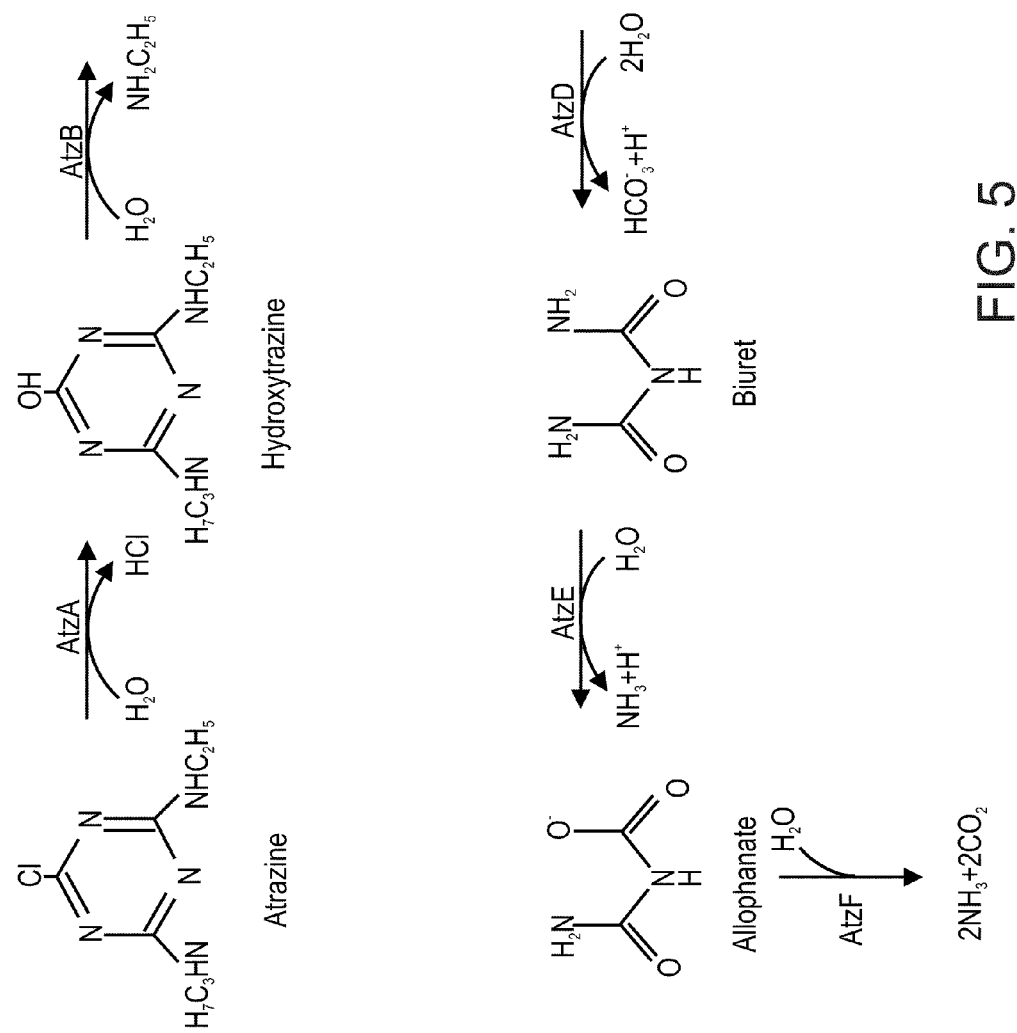

FIG. 5 depicts the degradation of atrazine by Pseudomonas ADP bacterial cells which are attached to (entrapped or encapsulated within) the microtube of the invention. Atrazine is degraded by the Pseudomonas ADP endogenous enzymes: atrazine chlorohydrolase, e.g., GenBank Accession No. NP_862474 (SEQ ID NO:1) encoded by the gene atzA, hydroxyatrazine hydrolase, e.g., GenBank Accession No. NP_862481 (SEQ ID NO:2) encoded by atzB, N-isopropylammelide isopropylamino hydrolase, e.g., GenBank Accession No. NP_862508 (SEQ ID NO:3) encoded by atzC, cyanuric acid amidohydrolase, e.g., GenBank Accession No. NP_862537 (SEQ ID NO:4) encoded by atzD, biuret hydrolase, e.g., GenBank Accession No. NP_862538 (SEQ ID NO:5) encoded by atzE and allophanate hydrolase, e.g., GenBank Accession No. AAK50333 (SEQ ID NO:6) encoded by atzF.

DESCRIPTION OF SPECIFIC EMBODIMENTS
OF THE INVENTION

The present invention, in some embodiments thereof, relates to methods of attaching a cell or a membrane-coated particle to a microtube and, more particularly, but not exclusively, to microtubes with cells or membrane-coated particles attached, entrapped or encapsulated therein and uses thereof in various purification, bioremediation, isolation, detection, and therapeutic applications.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

While reducing the present invention to practice, the present inventors have devised a method of attaching a cell or a membrane-coated particle to a microtube, to thereby obtain attached, entrapped or encapsulated cells or membrane-coated particles within the microtube.

Thus, as described in Example 1 of the Examples section which follows, the present inventors were capable of attaching cells (e.g., bacterial cells) to a microtube. In addition as shown in FIG. 2, cells attached within electrospun microtubes remained intact and viable. Moreover, as shown in Tables 4 and 5 and described in Example 2 of the Examples section which follows, the attached cells preserved their catalytic activity following the electrospinning process and were capable of degrading atrazine from a solution. These results suggest the use of the microtubes of some embodiments of the invention in various applications such a bioremediation of solutions (flow-through applications) and soils, purification, detoxification, and synthesis.

According to one aspect of the invention there is provided a method of attaching a cell or a membrane-coated particle-of-interest to a microtube, the method comprising: co-electrospinning two polymeric solutions through co-axial capillaries, wherein a first polymeric solution of the two polymeric solutions is for forming a shell of the microtube and a second polymeric solution of the two polymeric solutions is for forming a coat over an internal surface of the shell, the first polymeric solution is selected solidifying faster than the second polymeric solution and a solvent of the second polymeric solution is selected incapable of dissolving the first polymeric solution and wherein the second polymeric solution comprises the cell or the membrane-coated particle-of-interest, thereby attaching the cell or the membrane-coated particle-of-interest to the microtube.

As used herein the term "microtube" refers to a hollow tube having an inner diameter from about 50 nm to about 50 μm and an outer diameter from about 0.5 μm to about 100 μm.

According to some embodiments of the invention the inner diameter of the microtube shell of the invention can vary from about 100 nm to about 20 μm, e.g., from about 200 nm to about 10 µm, e.g., from about 500 nm to about 5 µm, e.g., from about 1 µm to about 5 µm, e.g., about 3 µm.

According to some embodiments of the invention the thickness of the microtube shell of the invention can vary from a few nanometers to several micrometers, such as from about 100 nm to about 20 µm, e.g., from about 200 nm to about 10 µm, from about 100 nm to about 5 µm, from about 100 nm to about 1 µm, e.g., about 500 nm.

According to some embodiments of the invention, the microtube may have a length which is from about 0.1 millimeter (mm) to about 20 centimeter (cm), e.g., from about 1-20 cm, e.g., from about 5-10 cm.

As used herein the term "cell" refers to a eukaryotic or prokaryotic cell.

According to some embodiments of the invention, the cell-of-interest comprises a cell wall. Non-limiting examples of cells which comprise a cell wall and which can be attached to the microtube of the invention include plant cells, bacteria (e.g., Gram positive and Gram negative bacteria), archaea, protozoa, fungi, and algae.

According to some embodiments of the invention, the cell-of-interest comprises a dermis (e.g., insect cells).

According to some embodiments of the invention, the cell has a diameter from about 500 nanometers to about 30 microns, e.g., from about 1-10 microns.

According to some embodiments of the invention, the cell has a diameter from about 1-2 microns.

The cell-of-interest which is attached to the microtube may have an activity (e.g., a catalytic activity or a binding activity) which is beneficial (e.g., expression of specific enzymes, e.g., atrazine-degrading enzyme, binding to a specific substrate via a cell receptor or via interaction with a molecule present in the cells, e.g., a DNA, RNA or protein). According to some embodiments of the invention, the cell is genetically modified to express a gene or a protein-of-interest (e.g., a mutant form which is capable of degrading a substrate with an improved catalytic activity as compared to a wild-type form; a specific label, e.g., a green fluorescent protein). Genetic modification can be done using known recombinant DNA technology and include, but not limited to, mutant isolation, know-out or knock-in mutagenesis, site-directed mutagenesis, gene silencing (e.g., siRNA, Ribozyme, DNAzyme, antisense) and gene overexpression (e.g., by transfection with an expression vector).

As used herein the phrase "membrane-coated particle" refers to a lipid membrane coated particle. The membrane may enable passage of molecules (e.g., organic and inorganic molecules, polymeric molecules) therethrough.

The membrane may be a naturally occurring membrane (e.g., a cell membrane), a portion of a naturally occurring membrane (e.g., a vesicle), an artificial membrane formed of natural membrane components (e.g., a liposome with a lipid bilayer), and/or an artificial membrane formed of non-natural components such as a polymer, a surfactant [e.g., dioleoylphosphatidylethanolamine (DOPE)], a ceramic, a glass and/or a metal.

Liposomes include emulsions, foams, micelles, insoluble monolayers, liquid crystals, phospholipid dispersions, lamellar layers and the like. The liposomes may be prepared by any of the known methods in the art [Monkkonen, J. et al., 1994, J. Drug Target, 2:299-308; Monkkonen, J. et al., 1993, Calcif. Tissue Int., 53:139-145; Lasic D D., Liposomes Technology Inc., Elsevier, 1993, 63-105. (chapter 3); Winterhalter M, Lasic D D, Chem Phys Lipids, 1993 September; 64(1-3):35-43]. The liposomes may be positively charged, neutral or negatively charged. The liposomes may have a single lipid layer or may be multilamellar. If the therapeutic agent is hydrophilic, its delivery may be further improved using large unilamellar vesicles because of their greater internal volume. Conversely, if the therapeutic agent is hydrophobic, its delivery may be further improved using multilamellar vesicles. Alternatively, the therapeutic agent (e.g. oligonucleotide) may not be able to penetrate the lipid bilayer and consequently would remain adsorbed to the liposome surface. In this case, increasing the surface area of the liposome may further improve delivery of the therapeutic agent. The liposomes can be non-toxic liposomes such as, for example, those prepared from phosphatidyl-choline phosphoglycerol, and cholesterol. The diameter of the liposomes used can range from 0.1-1.0 microns.

The particle may comprise an atom, an isotope, a molecule (e.g., a bio-molecule such as an amino acid, a nucleic acid, a polypeptide, a DNA or an RNA), a drug, a virus, a portion of a cell (e.g., a cell vesicle, enzymes of a cell), a bead (e.g., a glass bead, a magnetic bead) or any combination thereof, e.g., a magnetic bead conjugated to a molecule such as a polypeptide, a DNA and/or an RNA.

As used herein the term "attaching" refers to the binding of the cell or the membrane-coated particle-of-interest to the polymer(s) comprised in the microtube of the invention via covalent or non-covalent binding (e.g., via an electrostatic bond, a hydrogen bond, a van-Der Waals interaction) so as to obtain an absorbed, embedded or immobilized cell or membrane-coated particle-of-interest to the microtube of the invention.

According to some embodiments of the invention, the length (L) of the microtube can be several orders of magnitude higher (e.g., 10 times, 100 times, 1000 times, 10,000 times, e.g., 50,000 times) than the microtube's diameter (D). Accordingly, a cell or a membrane-coated particle-of-interest which is attached to a microtube is referred to as being entrapped or encapsulated within the microtube.

According to some embodiments of the invention, covalent attachment of the cell or membrane-coated particle can be via functional groups such as SH groups, amino groups, carboxyl groups which are added to the polymer(s) forming the microtube.

As used herein the phrase "co-electrospinning" refers to a process in which at least two polymeric solutions are electrospun from co-axial capillaries (i.e., at least two capillary dispensers wherein one capillary is placed within the other capillary while sharing a co-axial orientation) forming the spinneret within an electrostatic field in a direction of a collector. The capillary can be, for example, a syringe with a metal needle or a bath provided with one or more capillary apertures from which the polymeric solution can be extruded, e.g., under the action of hydrostatic pressure, mechanical pressure, air pressure and/or high voltage.

The collector serves for collecting the electrospun element (e.g., the electrospun microtube) thereupon. Such a collector can be a rotating collector or a static (non rotating) collector. When a rotating collector is used, such a collector may have a cylindrical shape (e.g., a drum), however, the rotating collector can be also of a planar geometry (e.g., an horizontal disk). The spinneret is typically connected to a source of high voltage, such as of positive polarity, while the collector is grounded, thus forming an electrostatic field between the dispensing capillary (dispenser) and the collector. Alternatively, the spinneret can be grounded while the collector is connected to a source of high voltage, such as with negative polarity. As will be appreciated by one ordinarily skilled in the art, any of the above configurations establishes motion of a positively charged jet from the spinneret to the collector. Reverse polarity for establishing motions of a negatively charged jet from the spinneret to the collector are also contemplated.

For electrospinning, the first polymeric solution is injected into the outer capillary of the co-axial capillaries while the second polymeric solution is injected into the inner capillary of the co-axial capillaries. In order to form a microtube (i.e., a hollow structure, as mentioned above), the first polymeric solution (which is for forming the shell of the microtube) solidifies faster than the second polymeric solution (also referred herein as a core polymeric solution, and is for forming a coat over the internal surface of the shell). In addition, the formation of a microtube also requires that the solvent of the second polymeric solution be incapable of dissolving the first polymeric solution.

The solidification rates of the first and second polymeric solutions are critical for forming the microtube. For example, for a microtube of about 100 µm, the solidification of the first polymer (of the first polymeric solution) can be within about 30 milliseconds (ms) while the solidification of the second polymer (of the second polymeric solution) can be within about 10-20 seconds. The solidification may be a result of polymerization rate and/or evaporation rate.

According to some embodiments of the invention, the solvent of the first polymeric solution evaporates faster than the solvent of second polymeric solution (e.g., the solvent of the first polymeric solution exhibits a higher vapor pressure than the solvent of the second polymeric solution).

According to some embodiments of the invention, the rate of evaporation of the solvent of the first polymeric solution is at least about 10 times faster than that of the solvent of the second polymeric solution. The evaporation rate of the solvent of the first polymeric solution can be at least about 100 times faster or at least about 1000 times faster than the evaporation rate of the solvent of second polymeric solution. For example, the evaporation of chloroform is significantly faster than the evaporation of an aqueous solution (water) due to the high vapor pressure at room temperature of the chloroform (195 mmHg) vs. that of the aqueous solution (23.8 mmHg).

When selecting a solvent of the second polymeric solution which is incapable of dissolving the first polymeric solution (i.e., a non-solvent of the first polymeric solution), the polymer of the first polymeric solution can solidify (e.g., through precipitation) and form a strong microtube shell which does not collapse, and which is characterized by an even thickness. According to some embodiments of the invention, the first polymeric solution (e.g., the solvent of the first polymer) is substantially immiscible in the solvent of the second polymeric solution.

The solvent of the second polymeric solution may evaporate while the polymer (of the second polymeric solution) forms a thin layer on the internal surface of the shell.

According to some embodiments of the invention, the solvent of the second polymeric solution is capable of evaporating through the internal surface of the shell.

The flow rates of the first and second polymeric solutions can determine the microtube outer and inner diameter and thickness of shell. Non-limiting examples are shown in Table 1 hereinbelow.

TABLE 1

Effect of the flow rates of the two polymeric solutions during electrospinning on microtube diameter and thickness of shell

| System No. | System: First polymeric solution/ Second polymeric solution | Flow rates (ml/hr) | R Outer Fiber radius (µm) | d Shell thickness (µm) | V Voltage (kV) | Electrostatic field kV/cm |
|---|---|---|---|---|---|---|
| M5 | First polymeric solution | 4 | 3.0-4.5 | 0.5 ± 0.1 | 8.5 | 0.43 |
|  | Second polymeric solution | 0.5 |  |  |  |  |
| M10 | First polymeric solution | 10 | 2.3-4.0 | 1.0 ± 0.1 | 8 | 0.5 |
|  | Second polymeric solution | 0.3 |  |  |  |  |
| M11 | First polymeric solution | 10 | 3-6 | 1.0 ± 0.1 | 9 | 0.56 |
|  | Second polymeric solution | 2 |  |  |  |  |

Table 1: Electrospinning was performed with the following solutions: First polymeric solution (for forming the shell) was 10% PCL in CHCl$_3$/DMF (8:2 weight/weight); second polymeric solution (for forming the coat) was 4% PEO in H$_2$O/EtOH (6:4, weight/weight). PCL 80K; PEO 600K.
The temperature during electrospinning was of 22-26° C.
The relative humidity was 58%, 52% and 53% for systems M5, M10 and M11, respectively.
The flow rates were measured in milliliter per hour (ml/hr); the outer microtube radius and the shell thickness were measured in microns (µm).
The resulting tubes were hollow (good tubes in systems M5 and M11, and mostly good in system M10).

As used herein the phrase "polymeric solution" refers to a soluble polymer, i.e., a liquid medium containing one or more polymers, co-polymers or blends of polymers dissolved in a solvent. The polymer used by the invention can be a natural, synthetic, biocompatible and/or biodegradable polymer.

The phrase "synthetic polymer" refers to polymers that are not found in nature, even if the polymers are made from naturally occurring biomaterials. Examples include, but are not limited to, aliphatic polyesters, poly(amino acids), copoly(ether-esters), polyalkylenes, oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, and combinations thereof.

Suitable synthetic polymers for use by the invention can also include biosynthetic polymers based on sequences found in naturally occurring proteins such as those of collagen, elastin, thrombin, fibronectin, or mutant or synthetic derivatives thereof or, starches, poly(amino acids), polypropylene fumarate), gelatin, alginate, pectin, fibrin, oxidized cellulose, chitin, chitosan, tropoelastin, hyaluronic acid, polyethylene, polyethylene terephthalate, poly(tetrafluoroethylene), polycarbonate, polypropylene and poly(vinyl alcohol), ribonucleic acids, deoxyribonucleic acids, polypeptides, proteins, polysaccharides, polynucleotides and combinations thereof.

The phrase "natural polymer" refers to polymers that are naturally occurring. Non-limiting examples of such polymers include, silk, collagen-based materials, chitosan, hyaluronic acid, albumin, fibrinogen, and alginate.

As used herein, the phrase "co-polymer" refers to a polymer of at least two chemically distinct monomers.

Non-limiting examples of co-polymers include, polylactic acid (PLA)-polyethyleneglycol (PEG), polyethylene glycol terephthalate (PEGT)/polybutylene terephthalate (PBT), PLA-polyglycolic acid (PGA), PEG-polycaprolactone (PCL) and PCL-PLA.

As used herein, the phrase "blends of polymers" refers to the result of mixing two or more polymers together to create a new material with different physical properties.

The phrase "biocompatible polymer" refers to any polymer (synthetic or natural) which when in contact with cells, tissues or body fluid of an organism does not induce adverse effects such as immunological reactions and/or rejections, cellular death, and the like. A biocompatible polymer can also be a biodegradable polymer.

According to some embodiments of the invention, the first and the second polymeric solutions are biocompatible.

Non-limiting examples of biocompatible polymers include polyesters (PE), PCL, calcium sulfate, PLA, PGA, PEG, polyvinyl alcohol, polyvinyl pyrrolidone, polytetrafluoroethylene (PTFE, teflon), polypropylene (PP), polyvinylchloride (PVC), polymethylmethacrylate (PMMA), polyamides, segmented polyurethane, polycarbonate-urethane and thermoplastic polyether urethane, silicone-polyether-urethane, silicone-polycarbonate-urethane collagen, PEG-DMA, alginate, hydroxyapatite and chitosan, blends and copolymers thereof.

The phrase "biodegradable polymer" refers to a synthetic or natural polymer which can be degraded (i.e., broken down) in a physiological environment such as by proteases or other enzymes produced by living organisms such as bacteria, fungi, plants and animals. Biodegradability depends on the availability of degradation substrates (i.e., biological materials or portion thereof which are part of the polymer), the presence of biodegrading materials (e.g., microorganisms, enzymes, proteins) and the availability of oxygen (for aerobic organisms, microorganisms or portions thereof), lack of oxygen (for anaerobic organisms, microorganisms or portions thereof) and/or other nutrients. Examples of biodegradable polymers/materials include, but are not limited to, collagen (e.g., collagen I or IV), fibrin, hyaluronic acid, polylactic acid (PLA), polyglycolic acid (PGA), polycaprolactone (PCL), polydioxanone (PDO), trimethylene carbonate (TMC), polyethyleneglycol (PEG), collagen, PEG-DMA, alginate, chitosan copolymers or mixtures thereof.

According to some embodiments, the polymeric solution can be made of one or more polymers, each can be a polymer or a co-polymer such as described hereinabove.

According to some embodiments of the invention, the polymeric solution is a mixture of at least one biocompatible polymer and a co-polymer (either biodegradable or non-biodegradable).

According to some embodiments of the invention, the first polymeric solution for forming the shell can be made of a polymer such as poly(e-caprolactone) (PCL), polyamide, poly(siloxane), poly(silicone), poly(ethylene), poly(vinyl pyrrolidone), poly(2-hydroxy ethylmethacrylate), poly(N-vinyl pyrrolidone), poly(methyl methacrylate), poly(vinyl alcohol), poly(acrylic acid), poly(vinyl acetate), polyacrylamide, poly(ethylene-co-vinyl acetate), poly(ethylene glycol), poly(methacrylic acid), polylactide, polyglycolide, poly(lactide-coglycolide), polyanhydride, polyorthoester, poly(carbonate), poly(acrylo nitrile), poly(ethylene oxide), polyaniline, polyvinyl carbazole, polystyrene, poly(vinyl phenol), polyhydroxyacid, poly(caprolactone), polyanhydride, polyhydroxyalkanoate, polyurethane, collagen, albumin, alginate, chitosan, starch, hyaluronic acid, and blends and copolymers thereof.

According to some embodiments of the invention, the second polymeric solution for forming the coat over the internal surface of the shell can be made of a polymer such as poly(acrylic acid), poly(vinyl acetate), polyacrylamide, poly(ethylene-co-vinyl acetate), poly(ethylene glycol), poly (methacrylic acid), polylactide polyglycolide, poly(lactide-coglycolide), polyanhydride, polyorthoester, poly(carbonate), poly(ethylene oxide), polyaniline, polyvinyl carbazole, polystyrene, poly(vinyl phenol), polyhydroxyacid, alginate, starch, hyaluronic acid, and blends and copolymers thereof.

During the formation of the microtube shell (e.g., following the solidification of the first polymeric solution) the second polymeric solution flows within the internal surface of the shell.

According to some embodiments of the invention, the second polymeric solution is selected capable of wetting the internal surface of the shell.

Various polymeric solutions are capable of wetting other polymeric surfaces (for forming the shell). Following is a non-limiting list of pairs of polymeric solutions in which the second polymeric solution is capable of wetting the internal surface of the shell formed by the first polymeric solution.

TABLE 2

Pairs of polymeric solutions for producing the microtube of the invention

| First polymeric solution forming the shell | Second polymeric solution capable of wetting the internal surface of the shell |
|---|---|
| 10% poly (e-caprolactone) (PCL); in chloroform ($CHCl_3$) and dimethylforamide (DMF) (80:20 by weight) | 4% poly(ethylene oxide) (PEO); in water ($H_2O$) and ethanol (60:40 by weight) |
| Nylon 6,6 in formic acid 7 to 12 wt % | 4% poly(ethylene oxide) (PEO); in water ($H_2O$) and ethanol (60:40 by weight) |
| Poly(L-lactide-co-glycolide) (PLGA 10:90) in hexafluroisopropanol (HFIP) concentrations ranging from 2 to 7 weight % solution. | 4% poly(ethylene oxide) (PEO) in water ($H_2O$) and ethanol (60:40 by weight) |
| Poly(L-lactide-co-glycolide) (PLGA 15:85) hexafluroisopropanol (HFIP) concentrations ranging from 2 to 7 weight % solution. | 4% poly(ethylene oxide) (PEO); in water ($H_2O$) and ethanol (60:40 by weight) |
| poly(lactide-co-glycolide) (PLGA; 1-lactide/glycolide__50/50) 1,1,1,3,3,3-hexafluoro-2-propanol (HFIP) concentrations ranging from 2 to 7 weight % solution. | 4% poly(ethylene oxide) (PEO); in water ($H_2O$) and ethanol (60:40 by weight) |

TABLE 2-continued

Pairs of polymeric solutions for producing the microtube of the invention

| First polymeric solution forming the shell | Second polymeric solution capable of wetting the internal surface of the shell |
|---|---|
| polyglycolide (PGA) in chloroform 3-10 weight % solution. | 9% poly(vinyl alcohol) (PVA); in water and ethanol (50:50 by weight) |
| poly(L-lactide) (PLA) in chloroform 3-10 weight % solution. | 9% poly(vinyl alcohol) (PVA); in water and ethanol (50:50 by weight) |
| Segmented polyurethane in DMF and THF (80:20 by weight) | 9% poly(vinyl alcohol) (PVA); in water and ethanol (50:50 by weight) |
| Polyurethane in DMF and tetrahydrofuran, THF (80:20 by weight) | 9% poly(vinyl alcohol) (PVA); in water and ethanol (50:50 by weight) |
| PLGA (poly lactic-co-glycolic acid); in chloroform and DMSO (dimethyl sulfoxide) in chloroform and DMSO (80:20 by weight). | 9% poly(vinyl alcohol) (PVA); in water and ethanol (50:50 by weight) |
| 10% PCL in CHCl$_3$/DMF (80:20 by weight) | 6% PEO in H$_2$O/EtOH (60:40 by weight) |
| 9% PCL in CHCl$_3$/DMSO (90:10 by weight) | 7% PEO in H$_2$O |
| 10% PCL in CHCl$_3$/DMF (80:20 by weight) | 9% PVA in ethanol/water (50:50 by weight) |
| 10% PCL 80 K CHCl$_3$:DMF (90:10 by weight) | 4% (w/w) PEO 600 K; in ethanol:H$_2$O (26:74 by weight) |
| 10% PCL 80 K +1% PEG 6 K CHCl$_3$:DMF (90:10 by weight) | 4% (w/w) PEO 600 K; in ethanol:H$_2$O (26:74 by weight) |

Table 2 (cont.). The polymers forming the solutions and the solvents are provided by weight ratios, i.e., a weight/weight (w/w) ratio.

According to some embodiments of the invention, the first and the second polymeric solutions are selected from the group consisting of: 10% poly(e-caprolactone) (PCL) in chloroform (CHCl$_3$) and dimethylforamide (DMF) (80:20 by weight) as the first polymeric solution and 4% poly(ethylene oxide) (PEO) in water (H$_2$O) and ethanol (60:40 by weight) as the second polymeric solution, 10% PCL in CHCl$_3$ and DMF (80:20 by weight) as the first polymeric solution and 6% PEO in water and ethanol (60:40 by weight) as the second polymeric solution, 9% PCL in CHCl$_3$ and DMF (90:10 by weight) as the first polymeric solution and 7% PEO in water as the second polymeric solution, 10% PCL in CHCl$_3$ and DMF (80:20 by weight) as the first polymeric solution and 9% poly(vinyl alcohol) (PVA) in water and:ethanol (50:50 by weight) as the second polymeric solution and 10% PCL in CHCl$_3$ and DMF (90:10 by weight) as the first polymeric solution and 4% (w/w) PEO in ethanol:water (26:74 by weight) as a second polymeric solution.

According to some embodiments of the invention, the microtube can be filled with a liquid.

To enable a flow of a liquid-of-interest within the microtube, i.e., along the coat polymer covering the internal surface of the shell (which originates from the second polymer solution), the surface (thin film) formed by the coat polymer should be designed such that it can be wetted by the liquid-of-interest. The ability to wet (wettability) polymer films by liquids is known in the art. For example, silicone oil or water can wet a surface made of a PEO polymer. The wettability of the coat polymer covering the internal surface of the shell can be controlled (e.g., improved) for example by attaching (e.g., using plasma treatment) functional groups such as hydroxyl groups (OH) which increase the hydrophilicity of the coat [see Thurston R M, Clay J D, Schulte M D, Effect of atmospheric plasma treatment on polymer surface energy and adhesion, Journal of Plastic Film & Sheeting 23 (1): 63-78 JAN 2007; which is incorporated within by reference].

For certain applications the microtube shell may comprise pores, thus creating a "breathing" tube. Methods of forming "breathing" microtube (i.e., microtubes with pores in the shell thereof) are described in PCT/IB2007/054001 to Zussman E., et al., which is fully incorporated herein by reference. Briefly, "breathing" tubes can be formed by the inclusion of a high percent (e.g., at least 80%) of a volatile component such as tetrahydrofuran (THF), chloroform, acetone, or trifluoroethanol (TFE) in the first polymeric solution forming the shell, and/or by the inclusion of a water-soluble polymer such as polyethylene glycol (PEG) in the first polymeric solution forming the shell so that the first polymeric solution comprises a blend of polymers in which one is water-soluble and the other is water-insoluble (e.g., a blend of PEG and PCL). Alternatively, "breathing" microtubes can be formed by inducing pores in the shell after the completion of the electrospinning process, essentially as described in PCT WO 2006/106506 to the present inventors, which is fully incorporated herein by reference, such as by passing an electrical spark or a heated puncturing element through the electrospun shell, or by using a pulsed or continuous laser beam through the electrospun shell.

According to some embodiments of the invention, the first polymeric solution comprises PEG for inducing pores in the shell. For example, to generate pores greater (>) than 150 nm in diameter, the first polymeric solution may include about 4% PEG MW 35 kDa. Similarly, to generate pores smaller (<) 150 nm in diameter, the first polymeric solution may include about 2% PEG MW 6 kDa.

The microtube shell can be designed for selective passage of certain molecules or particles. The passage through the shell pores depends on the size and/or the electrical charge of the molecules/particles with respect to the geometry (length and radius), surface energy, electrical charge of the shell pores, and the viscosity and surface tension of the liquid containing the molecules/particles.

According to some embodiments of the invention, the porosity [i.e., the ratio of the volume of the shell pores to the volume of the shell mass] and pore size can control the release of the cell or the membrane-coated particle-of-interest from the microtube. For example, a shell with pores larger than 1 μm in diameter (e.g., about 1-2 μm) can enable the release of a cell therethrough. In addition, increased porosity can result in a greater rate of release through the shell pores.

Alternatively, the microtube shell can be made such that it prevents diffusion or passage of the cell, the membrane-coated particle-of-interest or any molecule therethrough (e.g., substantially devoid of pores, or with pores having a diameter which is smaller than the cell or the membrane-coated particle-of-interest, or which exhibit a geometry which prevents passage of cells or membrane-coated particles therethrough).

According to some embodiments of the invention, the cell or the membrane-coated particle-of-interest is attached to the polymer of the coat over the internal surface of the shell. For example, as shown in FIG. 2 and described in Example 1 of the Examples section which follows, *Pseudomonas putida* cells which express the DsRed fluorescent protein were attached to the internal surface of the shell.

According to some embodiments of the invention, the cell or the membrane-coated particle is attached to the microtube shell.

According to some embodiments of the invention attachment of the cell (e.g., a eukaryotic cell such as a mammalian cell) or the membrane-coated particle is performed following microtube formation. For example, the microtube can be soaked with a solution containing the cell/membrane-coated particle. The cell/membrane-coated particle can diffuse through the shell pores and enter the inner lumen of the microtube. In addition, the microtube can be covalently attached to the cell/membrane-coated particle (e.g., via SH groups).

Regardless of the method of production, the present invention provides a microtube which comprises an electrospun shell, an electrospun coat over an internal surface of the shell and a cell or a membrane-coated particle-of-interest attached to the microtube.

As used herein, the phrase "electrospun shell" refers to a hollow element of a tubular shape, made of one or more polymers, produced by the process of electrospinning as detailed above.

As used herein the phrase "electrospun coat" refers to a thin layer covering the internal surface of the shell of the microtube of the invention which is made of one or more polymers by the process of electrospinning as detailed above.

One of ordinary skill in the art will know how to distinguish an electrospun object from objects made by means which do not comprise electrospinning by the high orientation of the macromolecules, the skin (e.g., shell) morphology, and the typical dimensions of the microtube which are unique to electrospinning.

The microtube of the invention can form an individual (e.g., single or separated) microtube or can form part of a plurality (e.g., an aligned array) of microtubes which can be either connected to each other or separated (as single, not-connected microtubes).

For the production of a single microtube a fork like clip is attached to the edge of the rotating disk. The disk is rotated for 1-2 seconds and individual microtubes are formed between the sides of the clip. In a similar way individual electrospun fibers were collected [see E. Zussman, M. Burman, A. L. Yarin, R. Khalfin, Y. Cohen, "Tensile Deformation of Electrospun Nylon 6,6 Nanofibers," *Journal of Polymer Science Part B: Polymer Physics*, 44, 1482-1489, (2006), herein incorporated by reference in its entirety].

Alternatively, when using a rotating collector, a plurality of microtubes can be formed and collected on the edge of the collector as described elsewhere for electrospun fibers [A. Theron, E. Zussman, A. L. Yarin, "Electrostatic field-assisted alignment of electrospun nanofibers", *Nanotechnology J.*, 12, 3: 384-390, (2001); herein incorporated by reference in its entirety].

The plurality of microtubes can be arranged on a single layer, or alternatively, the plurality of microtubes define a plurality of layers hence form a three dimensional structure. The microtubes can have a general random orientation, or a preferred orientation, as desired. For example, when the fibers are collected on a cylindrical collector such as a drum, the microtubes can be aligned predominantly axially or predominantly circumferentially. Different layers of the electrospun microtubes can have different orientation characteristics. For example, without limiting the scope of the present invention to any specific ordering or number of layers, the microtubes of a first layer can have a first predominant orientation, the microtubes of a second layer can have a second predominant orientation, and the microtubes of third layer can have general random orientation.

The microtube of the invention can be available as a dry fibrous mat(s) (e.g., as spun dry microtubes) or as a wetted mat(s) (e.g., following immersing or filling the microtube with a liquid).

According to some embodiments of the invention, the microtube which is attached to the cell or the membrane-coated particle-of-interest is configured as or in a microfluidics device. "Lab-on-a-chip" is described in a series of review articles [see for example, Craighead, H. "Future lab-on-a-chip technologies for interrogating individual molecules". Nature 442, 387-393 (2006); deMello, A. J. "Control and detection of chemical reactions in microfluidic systems". Nature 442, 394-402 (2006); El-Ali, J., Sorger, P. K. & Jensen, K. F. "Cells on chips". Nature 442, 403-411 (2006); Janasek, D., Franzke, J. & Manz, A. "Scaling and the design of miniaturized chemical-analysis systems". Nature 442, 374-380 (2006); Psaltis, D., Quake, S. R. & Yang, C. H. "Developing optofluidic technology through the fusion of microfluidics and optics". Nature 442, 381-386 (2006); Whitesides, G. M. "The origins and the future of microfluidics". Nature 442, 368-373 (2006); Yager, P. et al. "Microfluidic diagnostic technologies for global public health". Nature 442, 412-418 (2006)] each of which is fully incorporated herein by reference].

According to some embodiments of the invention, the liquid which fills in, flows in or surrounds the microtube enables the desorption (detachment) of the cell or the membrane-coated particle from the microtube (e.g., from the polymer included in the coat over the internal surface of the shell). According to of some embodiments of the invention the desorption process facilitates the interaction between the entrapped or encapsulated cell/membrane-coated particle with a molecule-of-interest (e.g., a substrate of an enzyme contained within the cell/membrane coated particle). According to some embodiments of the invention, the desorption process enables the flow and/or the release of the cell/membrane-coated particle within and from the microtube.

The cell or the membrane-coated particle-of-interest which is attached, entrapped or encapsulated within the microtube of the invention can be either an intact cell (i.e., having an un-ruptured membrane/cell wall) or non-intact cell (i.e., with a ruptured membrane/cell wall).

According to some embodiments of the invention, the cell or the membrane-coated particle-of-interest which is attached to, entrapped or encapsulated within the microtube of the invention maintains the activity, or at least a portion thereof, which it possessed prior to the attachment (e.g., of the same cell or the membrane-coated particle-of-interest prior to the electrospinning process, or when unattached to the microtube). For example, a bacterial cell with a ruptured cell wall/membrane may still contain the enzymatic activity of its proteins.

The term "activity" as used herein refers to any of a catalytic activity, kinetics, and/or affinity to a substrate or a ligand which the cell or the membrane-coated particle may have. Such an activity can be any biological activity such as catalysis, binding (with a specific affinity), hybridization, chelation, degradation, synthesis, catabolism, hydrolysis, polymerization, transcription, drug activity and the like.

As used herein the phrase "at least a portion of the activity" refers to at least about 10%, at least about 20-50%, e.g., more than about 50%, e.g., more than about 60%, e.g., more than about 70%, e.g., more than about 75%, e.g., more than about 80%, e.g., more than about 90%, e.g., more than about 95% of the activity which the cell or the membrane-coated particle possessed prior to the attachment to the microtube.

For example, as mentioned before and described in the Examples section which follows, the bacterial cells entrapped within the microtube of some embodiments of the invention preserved the specific activity to their substrates (atrazine).

The microtube of the invention with the attached, entrapped or encapsulated active cell or the membrane-coated particle-of-interest can be used in various applications which require the attachment of active cells (including portions thereof) or membrane-coated particles to a support and optionally also the controlled release therefrom.

According to some embodiments of the invention, the microtube of the invention is attached to more than one type of cells/membrane-coated particles. The microtube can be attached to a mixture of cells from several species or from a single species. The combination of cells can be selected according to the intended use. For example, several cells which are involved in complex reactions (e.g., processing of a substrate or a mixture of substrates) can be used.

According to some embodiments of the invention the microtube can be used as a micro-reactor (e.g., bioreactor) for chemical transition reactions [e.g., a multi-step reaction (cascade)] requiring high concentrations of several enzymes, e.g., enzymes produced by a certain cell (e.g., a bacterial cell) or by several cells or several different species (e.g., several types of bacterial cells).

According to an aspect of the invention, there is provided a method of processing a substrate-of-interest. The method is effected by contacting the substrate-of-interest with the microtube of the invention, wherein the cell or the membrane-coated particle which is attached to, entrapped or encapsulated within the microtube is capable of processing the substrate, thereby processing the substrate-of-interest.

As used herein the term "processing" refers to a catalytic activity performed by the cell or the membrane-coated particle which is attached to, entrapped or encapsulated within the microtube on its cognate substrate.

According to some embodiments of the invention processing involves enzymatic-dependent conversion (catalysis) of a substrate from a given chemical form to a distinct one. Examples of such catalysis reactions include, but are not limited to degradation, digestion, hydrolysis, nucleic acid cleavage, nucleic acid ligation, proteolytic cleavage, polymerization, transfer of an atom or functional group from one molecule to another and addition of a chemical group to a molecule.

According to some embodiments of the invention, such a process simply incorporates (endocytose) the substrate-of-interest such as for use in a reaction (synthesis) catalyzed by the cell or the membrane-coated particle.

According to some embodiments of the invention, the microtube can be used for the synthesis of rare biochemicals such as intermediates in biosynthesis pathways which are normally present at very low intracellular concentrations. For example, for the synthesis of indole glycerol phosphate the microtube according to some embodiments of the invention may be attached to a cell which expresses the enzymes participating in indole glycerol phosphate synthesis. For example, to accumulate indole glycerol phosphate the cell can be a mutant cell lacking the enzyme (or having a non-functional enzyme) converting indole glycerol phosphate to indole.

According to some embodiments of the invention, such a process can be the incorporation of the substrate-of-interest in a catabolism reaction catalyzed by the cell or membrane-coated particle which is attached, entrapped or encapsulated within the microtube.

For example, the catabolism reaction can be the degradation (e.g., by hydrolysis) of a toxic molecule for the purpose of detoxification (e.g., detoxifying water) or decomposition of an unwanted molecule.

According to an aspect of the invention there is provided a method of depleting a molecule from a composition containing the molecule, the method is effected by contacting the composition with the microtube of the invention, wherein the molecule is capable of binding to or being processed by the cell or the membrane-coated particle-of-interest, thereby depleting the molecule from the composition.

The composition containing the molecule may be in a liquid form (e.g., a solution), a solid form (e.g., soil) or a gel form. The molecule can be mixed with the composition or bound to the composition (by covalent or non-covalent bindings).

According to some embodiments of the invention, the method further comprising collecting the composition following the contacting.

As used herein the term "depleting" refers to removing an amount e.g., at least about 50%, at least about 60%, at least about 70%, at least about 80%, at least about 90%, at least about 95%, e.g., 99%, e.g., 100% of the molecule from the composition.

According to some embodiments of the invention, the depletion (removal) of the molecule from the composition is effected within a short time period, such as within minutes, hours or several days (e.g., about 1-7 days)

As used herein the phrase "contacting" refers to enabling the interaction between the molecule and the cell or the membrane-coated particle-of-interest which is attached to, entrapped or encapsulated within the microtube, for a time period which is sufficient for depleting the molecule from the composition (e.g., solution, soil). Such a contact can take place, for example, while the composition (e.g., solution) is passing through (e.g., via capillary forces) the end(s) of the hollow structure of the microtube and/or through the shell pores. Additionally or alternatively, such a contact between the molecule and the cell or the membrane-coated particle-of-interest can take place by incubating the microtube in the composition (e.g., by placing the microtube in a container including a solution, a soil or a gel)).

The solution can be a water-based or an oil-based solution which includes inorganic or organic molecules, such as a biological sample or a sample from a non-living source such as stream, industrial waste or ocean waters. As used herein the phrase "biological sample" refers to any sample derived from a living organism such as plant, bacteria or animals, and can include cells or alternatively be cell-free (i.e., include only a biological fluid).

According to some embodiments of the invention, the solution is an aqueous solution such as drinking water, groundwater and/or industrial waste water. According to some embodiments of the invention, the microtube of the invention forms part of an aqueous system designed for treatment of the aqueous solution (e.g., for depleting, eliminating or removing toxic moieties therefrom).

According to some embodiments of the invention, depleting is effected via bioremediation (i.e., the process of biodegradation and/or assimilation of a contaminant by microorganisms, fungi, green plants or their enzymes). Bioremediation can be used to remove contaminants such as soil contaminants, chlorinated hydrocarbons, crude oil herbicides, heavy metals, and the like.

According to some embodiments of the invention, depleting is effected via biodegradation.

As used herein the term "biodegradation" refers to degradation of a substrate using bio-molecules (e.g., enzymes) which are expressed by (or contained within) the cell or the membrane-coated particle which is attached to the microtube of the invention.

For example, to remove petroleum pollutants [e.g., aliphatics (e.g., C5-C36) and aromatics (e.g., C9-C22) such as benzene, toluene, ethylbenzene and xylenes (BTEX), phenol, naphthalene or certain hydrocarbons from oil] from water (biodegradation of petroleum pollutants), the microtube of the invention may be attached to bacteria utilizing alkanes as a sole source of carbon and energy or to membrane-coated particles including alkane-degrading enzymes. Such alkanes can be, for example, methane, ethane, propane, butane and mixtures thereof).

Non-limiting examples of butane-utilizing bacteria include Gram negative and Gram positive aerobic rods and cocci, facultative anaerobic Gram negative rods, non-photosynthetic, non-fruiting gliding bacteria and irregular non-sporing Gram positive rods. Of the Pseudomonadaceae family comprising Gram-negative aerobic rods and cocci, species of the following genera may be suitable: *Pseudomonas; Variovorax; Chryseobacterium; Comamonas; Acidovorax; Stenotrophomonas; Sphingobacterium; Xanthomonas; Frateuria; Zoogloea; Alcaligenes; Flavobacterium; Derxia; Lampropedia; Brucella; Xanthobacter; Thermus; Thermomicrobium; Halomonas; Alteromonas; Serpens; Janthinobacterium; Bordetella; Paracoccus; Beijerinckia*; and *Francisella*. Of the Nocardioform Actinomycetes family comprising Gram-positive Eubacteria and Actinomycetes, the following genera may be suitable: *Nocardia; Rhodococcus; Gordona; Nocardioides; Saccharopolyspora; Micropolyspora; Promicromonospora; Intrasporangium; Pseudonocardia*; and *Oerskovia*. Of the Micrococcaceae family comprising Gram-positive cocci, the following genera may be suitable: *Micrococcus; Stomatococcus; Planococcus; Staphylococcus; Aerococcus; Peptococcus; Peptostreptococcus; Coprococcus; Gemella; Pediococcus; Leuconostoc; Ruminococcus; Sarcina*; and *Streptococcus*. Of the Vibrionaceae family comprising facultative anaerobic Gram-negative rods, the following genera may be suitable: *Aeromonas; Photobacterium; Vibrio; Plesiomonas; Zymomonas; Chromobacterium; Cardiobacterium; Calymmatobacterium; Streptobacillus; Eikenella*; and *Gardnerella*. Of the Rhizobiaceae family comprising Gram-negative aerobic rods and cocci, the following genera may be suitable: *Phyllobacterium; Rhizobium; Bradyrhizobium*; and *Agrobacterium*. Of the Cytophagaceae family comprising non-photosynthetic, non-fruiting, gliding bacteria, the following genera may be suitable: *Cytophaga; Flexibacter; Saprospira; Flexithrix; Herpetosiphon; Capnocytophaga*; and *Sporocytophaga*. Of the Corynebacterium family comprising irregular, non-sporing Gram-positive rods, the following genera may be suitable: *Aureobacterium; Agromyces; Arachnia; Rothia; Acetobacterium; Actinomyces; Arthrobactera; Arcanobacterium; Lachnospira; Propionibacterium; Eubacterium; Butyrivibria; Brevibacterium; Bifidobacterium; Microbacterium; Caseobacter*; and *Thernoanaerobacter*.

Non-limiting examples of methane-utilizing bacteria include *Methylomonas* (e.g., *Methylomonas albus* such as the BG 8 strain; *Methylomonas methanica* such as the PM strain), *Methylobacter* (e.g., *Methylobacterium organophilum*), *Methylococcus* [e.g., *Methylococcus capsulatus*, such as the Texas strain ATCC 19069 and the Bath strain National Collection of Industrial Bacteria (NCIB) 11132], *Methylocystis* (*Methylocystis parvus*), and *Methylosinus* (e.g., *Methylosinus trichosporium* such as the OB 3b strain, e.g., NCIB No. 11131 and The Fermentation Research Institute (FR1), Japan (as FERM-P4981)].

For example, for the biodegradation of cyanide [depletion of cyanide from a solution such as industrial waste water (e.g., of silver mining)], bacterial cells or membrane-coated particles capable of degrading free ($CN^-$ or HCN) or complexed (e.g., metal-cyanide complex) cyanide can be attached to the microtube of the invention. For example, degradation of free cyanide can be performed using the archeae bacterium *Sulfolobus* which is also used in gold extraction from low grade minerals [see Knowles, C. J. and Bunch, A. W., "Microbial cyanide metabolism. Advances in Microbial Physiology", (1986); 27: 73 111]; Complexed cyanide such as silver-cyanide [$Ag(CN)_2$] can be degraded using the *Citrobacter* sp. MCM B-181, *Pseudomonas* sp. MCM B-182, *Pseudomonas* sp. MCM B-183 and *Pseudomonas* sp. MCM B-184 bacteria [see Patil Y B, Paknikar K M, Letters in Applied Microbiology, (2000), 30: 33-37] which utilize metal-cyanide complexes as a nitrogen source and release ammonia and carbon dioxide as degradation products.

To remove toxic moieties of herbicides that enters the water supply, such as the chlorine entity of atrazine (biodegradation of atrazine), a microtube which includes cells or membrane-coated particles (e.g., portions of cells, liposomes) capable of degrading atrazine can be used. For example, bacterial cells or portions of cells including the atrazine degrading enzymes: atrazine chlorohydrolase, hydroxyatrazine hydrolase, N-isopropylammelide isopropylamino hydrolase, cyanuric acid amidohydrolase, biuret hydrolase, and allophanate hydrolase (FIG. 5) can be used. Such bacteria can be the *Pseudomonas* ADP (which endogenously express the ATZ genes) or any other bacterial strain which exogenously express the ATZ genes (atzA-atzF genes), such as the *Pseudomonas putida* S12 described in the Examples section which follows.

For example, as described in Tables 4 and 5 and Example 2 of the Examples section which follows, efficient atrazine degradation was achieved by microtubes which were attached to the *Pseudomonas* ADP or *Pseudomonas putida* S12 that express the atzA-atzF genes.

According to some embodiments of the invention, biodegradation of atrazine is effected such that more than about 50%, e.g., more than about 60%, e.g., more than about 70%, e.g., more than about 80% of atrazine is removed from a solution containing about 20 mg atrazine per liter following 1-4 days of contacting the solution with the microtube. According to exemplary embodiments of the invention, biodegradation of atrazine is effected such that more than about 90%, more than about 95%, e.g., 100% of atrazine is removed from a solution containing about 20 mg atrazine per liter following 1-2 days of contacting the solution with the microtube.

As mentioned hereinabove, the microtube of the invention may form part of an aqueous system designed for treatment of the aqueous solution.

FIG. 4 schematically illustrates a single configuration of a bioremediation system generated according to some embodiments of the invention. System 300 comprises conduit [220, e.g., part of an aqueous system, can be a plastic or metal (e.g., copper) pipe/tube] having borders (100) includes microtube (230) with shell borders (120) and entrapped bacterial cells (210). For purification (e.g., detoxification of water), a liquid (e.g., drinking water) containing molecule (150) flows within the conduit. Pores (180) within the microtube shell enable the diffusion of molecule (150) through the microtube shell to the microtube lumen (140) containing bacterial cells (210). Cells (210) interact with molecule (150) and reaction product (160) diffuses out of the microtube outside of the microtube lumen (140) through the microtube shell pores (180).

According to some embodiments of the invention, a microtube with entrapped bacterial cells expressing the atrazine degrading enzymes is placed (or packed within) a column [e.g., conduit (220) as shown in FIG. 4] filled with an aqueous solution (e.g., drinking water). The small diameter of the microtube (e.g., 3-5 μm) and the significant length (e.g., 20 cm) provides an enormous surface area for degrading atrazine. As mentioned above, due to the dimensions of the microtube (wherein the length is several orders of magnitude larger than the diameter), the cells are entrapped within the microtube and are not washed away. Accordingly, there is no need to add a carbon source to the bacterial cells.

According to some embodiments of the invention, the cells entrapped within the microtube can continue to degrade atrazine for an extended time period without the formation of a biofilm (i.e., a complex aggregation of microorganisms marked by the excretion of a matrix). According to some embodiments of the invention, the microtube shell prevents passage of predators such as Bdellovibrios, protozoa, and bacteriophage thus protecting the entrapped bacterial cells from such predators.

According to some embodiments of the invention, the bacterial cells may be refreshed by immersing the microtube in growth medium which contains usable carbon, nitrogen, phosphorus and sulfur sources and thereby both allowing the cells to proliferate and/or renew their metabolic potential.

According an aspect of the invention, there is provided a method of isolating a molecule from a solution. The method is effected by (a) contacting the solution with the microtube of the invention under conditions which allow binding of the molecule to the cell or the membrane-coated particle-of-interest, and; (b) eluting the molecule from the microtube; thereby isolating the molecule from the solution.

As used herein the term "isolating" refers to physically separating the molecule from the solution or its other components by binding the molecule to the cell or membrane-coated particle which is attached to, entrapped or encapsulated within the microtube and eluting the bound molecule therefrom. As used herein the term "eluting" refers to dissociating the bound molecule from the microtube. Those skilled in the art are capable of adjusting the conditions required for eluting (e.g., releasing) the molecule from the microtube and/or separating the molecule from the cell or membrane-coated particle.

According to an aspect of the invention, there is provided a method of detecting a presence of a molecule in a sample. The method is effected by (a) contacting the sample with the microtube of the invention, wherein the cell or the membrane-coated particle-of-interest is capable of binding to or processing the molecule, and (b) detecting the binding or the processing; thereby detecting the presence of the molecule in the sample.

As used herein the phrase "detecting binding or the processing" refers to identifying a change in the concentration, conformation, spectrum or electrical charge of the molecule in the sample and/or of the cell or membrane-coated particle that is attached to the microtube following the binding therebetween or following the processing of the molecule by the cell or the membrane-coated particle. Identification of the binding or processing can be performed using methods known in the art such as following the fluorescence or the color of the sample, radioactivity of the sample, the electrical conductivity of the sample and the like. Binding of a molecule to a cell may be via a specific receptor on the cell.

According to some embodiments of the invention, the cell or the membrane-coated particle-of-interest which is attached to the microtube is labeled or comprises a label [e.g., by genetic modification as described above, or by conjugation to a dye, fluorophore, radio-isotope, or an enzyme (e.g., horse radish peroxidase) capable of producing a colorimetric product], and detecting the binding or processing of a molecule is performed by following such a label.

The microtube according to some embodiments of the invention can be used as a biosensor, for the detection of molecules in a sample. Such a biosensor can be advantageous over known open field biosensors (e.g., sensors in which the cell or membrane-coated particle is conjugated to a solid support not having a tubular structure, such as a flat support) especially due to the increased ratio between the size of the microtube surface (which attaches the cell/membrane-coated particle) and the volume of the sample being in contact therewith.

The microtube according to some embodiments of the invention can be used to release the attached cell or membrane-coated particle through pores in the shell or the microtube openings (i.e., the ends of the tubular structure). According to some embodiments of the invention, the microtube can be placed in a supercritical fluid (e.g., liquid nitrogen) for a short period of time (e.g., 2-10 minutes), following which the microtube is cut (e.g., with a sharp knife, razor blade) close to its end. The microtube can be also subject to cross linking using, e.g., glutaraldehyde which assists in preserving the openness of the microtube.

The microtube according to some embodiments of the invention can be attached to bacteria that produce and contain nano-magnets. Such bacteria were discovered and isolated more than 30 years ago (Blakemore, R 1975 Magnetotactic bacteria. Science 190:377-379; Bayzlinski, D. A., Frankel, R. B. and Jannasch, H. W. 1989 Anaerobic magnetite production by marine, magnetotactic bacteria. Nature 334:518-519). Some of these strains contain a string of magnets whose poles, N and S, are aligned. Without being bound by any theory, during the electrospinning process and the flow of the second polymeric solution the bacteria can be oriented such that their long axis is parallel to that of the microtube (see an example of rod bacteria aligned within the microtube; FIG. 2). When using bacteria that contain magnets, the bacteria can be aligned by applying magnetic force and their tendency to be aligned by flow such that the attached bacteria are aligned in a polar manner where all their N's face in the same direction.).

Microtubes with attached magnet producing bacteria can be used in industry (e.g., microelectonics) and medical applications (such as imaging).

The microtube according to some embodiments of the invention can be used in medical dialysis to remove materials from blood and other bodily fluids such as urine.

The microtube of some embodiments the invention can be used in various ex vivo and in vivo applications. For example, the microtube can be attached to cells (e.g., mammalian) capable of inducing tissue formation [e.g., stem cells such as adult stem cells (tissue stem cells) or embryonic stem cells]. Briefly, the microtube can be contacted with a medium (e.g., tissue culture medium, physiological solution, blood) which is suitable for proliferation, differentiation and/or migration of the cell so as to enable tissue formation.

The microtube of some embodiments of the invention (e.g., a microtube made of biocompatible polymers) can be implanted in a subject in need thereof.

As used herein the phrase a "subject in need thereof" refers to any animal subject e.g., a mammal, e.g., a human being which suffers from a pathology (disease, disorder or condition) which can be treated by the cell/membrane coated particle which is attached, entrapped or encapsulated within the microtube of the invention.

The term "treating" as used herein refers to inhibiting, preventing or arresting the development of a pathology and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

According to some embodiments of the invention, the microtube is implanted in a subject to induce in vivo formation of a tissue.

According to some embodiments of the invention, the microtube directs the attached (or entrapped) cell or membrane-coated particle-of-interest (e.g., a drug in a liposome) to a target tissue of a subject (e.g., targeted delivery of a drug).

Methods of implanting grafts such as the microtube of the invention into a subject are known in the art. For example, the microtube can be implanted subcutaneously, intradermally, or into any body cavity (e.g., abdomen), as well as into the vascular system (using e.g., a hollow catheter delivery system). Alternatively, the microtube of the invention can be connected to a body conduit (e.g., a blood vessel such as a vein or an artery) such that it enables the flow of a fluid therethrough.

The invention further envisages the use of the microtube of the invention, which includes a cell or a membrane-coated particle-of-interest attached thereto, for guiding cell growth ex vivo or in vivo. For example, neuronal cells which are attached or entrapped within the microtube can be contacted with solution containing growth factors and/or nutrients needed for neuronal growth. It will be appreciated that once an initial neuronal growth has occurred ex vivo, such a system (i.e., the microtube with the neuronal cells) can be implanted in a subject in need thereof (e.g., a subject with degenerated, damaged or injured neuronal cells) to thereby enable neuronal growth and guidance.

The microtube of some embodiments of the invention can be included in a kit/article of manufacture along with a packaging material and/or instructions for use in any of the above described methods or applications.

The methods described herein may be conducted batch-wise.

It will be appreciated that the microtubes of the some embodiments of the present invention can find wide use in waste, commodity, food, agrotec, cosmetic and pharma industries. A detailed discussion of some embodiments is not meant to be limiting.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Methods

Eletrospinning solutions: The compositions of the shell and core solutions are given in Table 3, hereinbelow. All polymers and solvents were purchased from Sigma-Aldrich and were used as is.

Bacterial cells and growth medium—*Pseudomonas putida* S12 (exogenously expressing atz genes by transfection with a plasmid including the coding sequences of the atz genes depicted in FIG. 5) and *Pseudomonas* ADP (which endogenously express the atz genes), both of which are capable of degrading atrazine and using it as a source of nitrogen, were grown to stationary phase in an ATZ culture medium (modified from Mandelbaum R. T., Wackett L. P., Allan D. L., 1993. "Mineralization of the s-triazine ring of atrazine by stable bacterial mixed cultures". Applied and Environmental Microbiology 59: 1695-1701) in which atrazine was included as the sole source of nitrogen. The ATZ culture medium was prepared as follows: For each liter of double distilled water the following were added: $KH_2PO_4$ 1.6 grams, $K_2HPO_4$ 0.4 grams, $MgSO_4.7H_2O$ 0.2 grams, NaCl 1 gram, $CaCl_2$ 25 mg and citrate (sodium-citrate) 2 g; 20 mg atrazine; 20 ml of a vitamin and trace element stock solution. The vitamin and trace element stock solution contains per liter: Nitrilotriacetic acid 10 grams, KOH 7.3 grams, $MgSO_4.7H_2O$ 14.45 grams, $(NH_4)_6Mo_7O_{24} \times 4H_2O$ 9.25 grams, $FeSO_4 \times 7H_2O$ 100 mg, nicotinic acid 50 mg, biotin 0.5 mg, thiamin HCl 2.5 mg, and 44 metal solution 50 ml. 44 metal solution contains per 100 ml: EDTA 250 mg, $ZnSO_4$ $7H_2O$ 1.1 grams, $FeSO_4$ $7H_2O$ 0.5 grams, $MnSO_4H_2O$ 154 mg, $CuSO_4$ $5H_2O$ 50 mg, $Co(NO_3)_2$ $6H_2O$ 75 mg, $Na_2B_4O_7$ $10H_2O$ 20 mg.

The bacterial cells ($10^9$ cells/ml) grown in the above medium were added to the core solution (e.g., PEO in water or PEO+40% ethanol) (e.g., at a ratio of 9:1 (volume/volume) core solution to cells) and electrospinning was performed using the shell and core solutions shown in Table 3, hereinbelow, so as to form a microtube in which the bacterial cells are attached to the internal surface (coat) of the shell. The presence and localization of the bacterial cells following formation of the microtube was determined using a fluorescence microscope.

TABLE 3

Two types of core-shell microtubes: composition of the solutions

| Type | Shell solution | Core solution |
|---|---|---|
| 1 | 10% PCL 80 K; in $CHCl_3$:DMF (90:10 by weight) | 4% (w/w) PEO 600 K in ethanol:$H_2O$ (26:74 by weight) and bacterial cells ($10^9$ cells/ml) in a 10:1 ratio (900 μl of polymer solution and 100 μl of bacterial cell) |
| 1 | 9% PCL 80 K; in $CHCl_3$:DMSO (90:10 by weight) | 8% (w/w) PEO 600 K in water + bacterial cells ($10^9$ cells/ml) in a 10:1 ratio (900 μl of polymer solution and 100 μl of bacterial cell) |
| 2 | 10% PCL 80 K + 1% PEG 6 K; in $CHCl_3$:DMF (90:10 by weight) | 4% (w/w) PEO 600 K in ethanol:$H_2O$ (26:74 by weight) + bacterial cells ($10^9$ cells/ml) in a 10:1 ratio (900 μl of polymer solution and 100 μl of bacterial cell) |

Table 3. Microtubes were formed by co-electrospinning of the shell solution (a first polymeric solution for forming the shell) and a core solution (a second polymeric solution for forming the coat over the internal surface of the shell). Type 1 microtubes - do not include PEG in the shell solution; Type 2 microtubes - include PEG in the shell solution.

Electrospinning—Hollow microtubes (core-shell hollow fibers) were fabricated by a co-electrospinning process using the set up described by Sun et al. (2003) and Zussman et al. (2006) with the polymeric solutions (for forming the shell and coat over the internal surface of the shell) as described in Table 3 above. All experiments were conducted at room temperature (about 22° C.) and a relative humidity of about 35%. The spinning parameters were as follow: the electrostatic field used was approximately 0.44 kV/cm and the distance between the spinneret and collector plate was 16 cm. The flow rates of both the core and shell solutions were controlled by two syringe pumps and were 3.5 ml/hour for the shell solution and 1 ml/hour for the core solution. The fibers were collected as a strip on the edge of a vertical rotating wheel (Theron A., et al., (2001)) having a velocity of 1.2 m/second. For fluorescence microscopy, a few fibers were collected directly onto a microscope slide.

Imaging—Images of the fibers were obtained using a Leo Gemini high resolution scanning electron microscope (HRSEM) at an acceleration voltage of 3 kV and a sample to detector distance of 3-5 mm. The specimens were coated with a thin gold film to increase their conductivity. Fluorescence microscope Leica D M IRE2 at excitation and emission wave lengths of 359 and 361 nm, respectively, was used for the imaging of fibers filled with fluorescent product.

Measurement of Atrazine degradation—The mat containing the entrapped bacterial cells was immersed in a medium

[ATZ-containing phosphate buffer (20 mg Atrazine per liter of phosphate buffer)] and following predetermined time periods (e.g., 1 to 6 days) aliquots from the medium surrounding the mat(s) were taken and the amount of atrazine was measured using HPLC. The aliquots were mixed with an equal volume of methanol and were centrifuged for 10 minutes at 10,000×g to remove salts and other insoluble materials. High-performance liquid chromatography (HPLC) was conducted on Hewlett Packard HPLC(HP110 series). Separation was done at a flow rate of 0.6 ml/minute on a LiChrospher 100 RP-18 (5 μm) column (LiChroCART HPLC Cartridge system 250-4; Merck, Darmstadt, Germany), using 200 mM $NH_4CH_3COO$ in 70:30% [volume/volume (v/v)] methanol/water as a mobile phase. Concentration of atrazine was quantified relative to authentic standard by integrating peak area at 220 nm.

Example 1

Entrapment of Bacterial Cells within Microtubes

Experimental Results

Attachment of bacterial cells within an electrospun microtube—A microtube with cells entrapped therein was formed by co-electrospinning of the two polymeric solutions: 9% [weight/weight (w/w)] polycaprolactome (PCL) dissolved in chloroform/DMSO (9:1; w/w) as a first polymeric solution (for forming the shell); and 8% poly(ethylene oxide) (PEO) in water as second polymeric solution (for forming the coat over the internal surface of the shell) which also included *Pseudomonas putida* or *Pseudomonas* ADP bacterial cells (at a concentration of $10^9$ cells/ml) at a ratio of 9:1 [volume/volume (v/v); 900 μl polymeric solution and 100 μl of bacterial cells]. The *Pseudomonas putida* S12 cells had been previously transformed to express the DsRed fluorescent protein (GenBank Accession No. Q9U6Y8, SEQ ID NO:7), such that following microtube formation, the red fluorescence originating from the *Pseudomonas putida* cells can be observed using a fluorescence microscope. As is shown in FIG. 2, the *Pseudomonas putida* cells were entrapped within the electrospun microtube. In addition, the observed red fluorescence demonstrates that the cells were intact.

Example 2

Atrazine Degradation Using Bacterial Cells Entrapped within the Microtube

Experimental Results

Degradation of atrazine using bacterial cells which are entrapped within the microtube of the invention—*Pseudomonas putida* S12 or *Pseudomonas* ADP, both of which are capable of degrading atrazine and using it as a source of nitrogen, were grown to stationary phase in a medium in which atrazine was included as the sole source of nitrogen. The cells were added to the core solution [e.g., 4% PEO in 40% ethanol (w/w); or 8% PEO in water (w/w)] and electrospun with the shell-forming solution (without the addition of PEG to the shell solution) to render microtubes with a core-shell structure. The microtubes (2 types for each strain) were tested for their ability to degrade atrazine. The microtubes were immersed in a flask containing phosphate buffer with atrazine (20 mg atrazine in 1 liter of phosphate buffer) and degradation was followed by examining the amount of residual atrazine using HPLC (conducted on Hewlett Packard HPLC, HP110 series), in aliquots taken at predetermined time periods (from one day to several days). The microtubes were then transferred to a new flask and the procedure repeated.

The percentages of atrazine removal following incubation of the *Pseudomonas* ADP cells—containing microtubes in ATZ-containing phosphate buffer are summarized in Table 4, hereinbelow.

TABLE 4

Degradation of atrazine by electrospun microtubes containing *Pseudomonas* ADP

| Days from beginning of experiment | Transfer No. | Incubation time in ATZ culture medium (days) before transfer | % Atrazine removal using microtubes with solution A as core | % Atrazine removal using microtubes with solution B as core |
|---|---|---|---|---|
| 0 | 1 | 1 | 59.0 | 32.3 |
| 1 | 2 | 2 | 51.8 | 20.8 |
| 3 | 3 | 3 | 87.9 | 94.0 |
| 6 | 4 | 1 | 76.5 | 91.5 |
| 7 | 5 | 2 | 91.2 | 94.3 |
| 14 | 6 | 6 | 85.0 | 85.0 |
| 15 | 7 | 1 | 96.0 | 96.0 |
| 16 | 8 | 1 | 94.2 | 94.5 |
| 17 | 9 | 3 | 100.0 | 100.0 |
| 20 | 10 | 1 | 100.0 | 100.0 |
| 21 | 11 | 2 | 97.5 | 97.5 |

Table 4: The degradation of atrazine by electrospun microtubes containing *Pseudomonas* ADP bacterial cells. Shown are the percentages of atrazine removal following predetermined incubation periods of microtubes with entrapped *Pseudomonas* ADP bacterial cells in a phosphate buffer which contains ATZ (20 mg atrazine per liter). The core solutions used for forming the microtube coat over the internal surface of the shell were: solution A - 4% PEO in 40% ethanol; and solution B - 8% PEO in water.

As shown in Table 4, hereinabove, when a microtube which was prepared with a core solution containing 4% PEO in 40% ethanol was used, efficient removal of atrazine (e.g., about 95% removal) was observed throughout the experiment and the entrapped bacterial cells within the microtubes continued to remove atrazine even after 11 transfers. When a microtube which was prepared with a core solution containing 8% PEO in water was used, efficient removal of atrazine (e.g., about 95% removal) was observed throughout the time of the experiment and the microtube preparation (with entrapped cells) remained competent in this regard even after 21 days and 11 transfers.

Microtubes with attached cells were incubated ATZ growth medium (for 4 days, 30° C.), and then the microtubes were transferred to ATZ-containing phosphate buffer for the beginning of experiment.

The percentages of atrazine removal following incubation of the *Pseudomonas putida* S12 bacterial cells—containing microtubes in an ATZ-containing phosphate buffer are summarized in Table 5, hereinbelow.

TABLE 5

Degradation of atrazine by electrospun microtubes containing *Pseudomonas putida* S12

| Days from beginning of experiment | Transfer No. | Incubation time in ATZ culture medium (days) before transfer | % Atrazine removal using microtubes with 5% PEO in water as a core solution |
|---|---|---|---|
| 0 | 1 | 4 | 100 |
| 4 | 2 | 3 | 100 |
| 7 | 3 | 2 | 100 |
| 9 | 4 | 2 | 100 |
| 11 | 5 | 3 | 100 |

TABLE 5-continued

Degradation of atrazine by electrospun microtubes
containing Pseudomonas putida S12

| Days from beginning of experiment | Transfer No. | Incubation time in ATZ culture medium (days) before transfer | % Atrazine removal using microtubes with 5% PEO in water as a core solution |
|---|---|---|---|
| 16 | 6 | 2 | 98.3 |
| 21 | 7 | 5 | 100 |

Table 5: The degradation of atrazine by electrospun microtubes containing *Pseudomonas putida* S12 bacterial cells. Shown are the percentages of atrazine removal following predetermined incubation periods of microtubes with entrapped S12 bacterial cells in a phosphate buffer which contains ATZ (20 mg atrazine per liter). The core solution used for forming the microtube coat over the internal surface of the shell was 5% PEO in water.

As shown in Table 5, hereinabove, 100% removal of atrazine from the solution was observed following 4 days incubation of the S12-containing microtubes of the invention in the ATZ-containing phosphate buffer. Efficient removal of atrazine continued through seven transfers and remained complete in microtube material to the 21$^{st}$ day.

This is a new and efficient way to remove atrazine from water in e.g., a continuous flow system composed of columns filled with electrospun hollowfibers containing suitable bacterial cells (e.g., which are capable of degrading atrazine). Thus, the influent water which contains atrazine penetrates (e.g., by diffusion) into the hollow fibers (the microtubes) and the atrazine is broken down to non-toxic material, such that the effluent water is free of atrazine.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Additional References are Cited in Text (1) Reneker, D. H., Yarin, A. L., Zussman, E., Xu, H. "Advances in Applied Mechanics" (2006), 40.
(2) Ramakrishna, S., Fujihara, K., Teo, W.-e., Lim, T. C., Ma, Z. "An Introduction to Electrospinning and Nanofibers", 1 ed., World Scientific Publishing Company, (2005).
(3) Li, D. Xia, Y. N. Advanced Materials 2004, 16, 1151.
(4) Salalha W, Kuhn J, Dror Y, Zussman E, "Encapsulation of bacteria and viruses in electrospun nanofibers". Nanotechnology, (2006) 17:4567-4575.
(5) Brayner R, Barberousse H, Hemadi M, Djedjat A, Yepremian C, Coradin T, Livage J, Fievet F, Coute A, "Cyanobacteria as bioreactors for the synthesis of Au Ag Pd and Pt nanoparticles via an enzyme-mediated route". J Nanosci Nanotechnol, (2007) 7:2696-2708.
(6) Moat A G, Foster J W, Microbial Physiology pp. 360-363, (1995). Wiley-Liss, New York, Chichester, Brisbane, Toronto, Singapore;
(7) Doelle H W, Bacterial Metabolism, Chapter 9: Pseudomonadaceae. Academic Press, New York, London, (1969);
(8) van der Linden A C, Thijsse G J E, "The mechanisms of microbial oxidations of petroleum hydrocarbons". Advances in Enzymology, (1965) 27:469;
(9) Herzberg M, Desoretz C G, Kuhn J, Klein S, Green M, "Visualization of active biomass distribution in a BGAC fluidized bed reactor using GFP tagged *Pseudomonas putida* F1". Water Res. (2006) 40:2704-2712;
(10) Kita Y, Nishikawa H, Takemoto T, "Effect of cyanide and dissolved oxygen concentration on biological Au recovery". J Biotechnol., (2006) 124:545-551;
(11) Tsuruta T, "Biosorption and recycling of gold using various microorganisms". J Gen Appl Microbiol., (2004) 50:221-228;
(12) Karhikeyan S, Beveridge T J, "*Pseudomonas aeruginosa* biofilms react with and precipitate toxic soluble gold". Environ Microbio, (2002) 4:667-675;
(13) Savvaidis I, "Recovery of gold from thiourea solutions using microorganisms". Biometals, (1998) 11:145-151;
(14) Li J, Jin Z, "Isolation and determination of silver-resistant bacteria plasmids". Ying Yong Sheng Tai Xue Bao, (2006) 17:305-308;
(15) Patil Y B, Paknikar K M, "Biodetoxification of silver-cyanide from electro plating industry". Lett Appl Microbiol, (2000) 30:33-37;
(16) Yoon K P, Misra T K, Silver S, "Regulation of the cadA cadmium resistant determinant of *Staphylococcus aureus* plasmid p1258". J Bacteriol, (1991) 173:7643-7649;
(17) Summers A O, Jacoby G A, "Plasmid resistance to tellurium compounds". J Bacteriol, (1977) 129:278-281;
(18) Flemming C A, Ferris F G, Beveridge T J, Bailey G W, "Remobilization of toxic heavy metals adsorbed to bacterial wall-clay composites". Appl Environ Microbiol, (1990) 56:3191-3203;
(19) Mullen M D, Wolf D C, Ferris F G, Beveridge T J, Flemming C A, "Bacterial sorption of heavy metals". Appl Environ Microbiol, (1989) 55:3143-3149;
(20) Rashamuse K J, Whiteley C G, "Bioreduction of Pt (IV) from aqueous solutiojn using sulphate-reducing bacteria". Appl Microbiol Biotechnol, (2007) 75:1429-1435;
(21) Yong P, Paterson-Beedle M, Mikheenko I P, Macashie L E, "From biomineralization to fuel cells: biomanufacture of Pt and Pd nanocrystals for fuel cell electrode catalyst". Biotechnol Lett, (2007) 29:539-544;
(22) Sun, Z.; Zussman, E.; Yarin, A. L.; Wendorff, J. H.; Greiner, A. Adv. Mater. (2003), 15, 1929-1932.

What is claimed is:

1. A microtube comprising:
   an electrospun shell,
   an electrospun coat polymer over an internal surface of said shell and a cell or a membrane-coated particle-of-interest attached to the microtube,
   wherein said electrospun shell is formed of a first polymeric solution comprising a first solvent and said electrospun coat is formed of a second polymeric solution comprising a second solvent,
   wherein said second solvent of said second polymeric solution is incapable of dissolving the polymer of said first polymeric solution,
   wherein said first polymeric solution solidifies faster than said second polymeric solution,
   wherein said second polymeric solution is capable of wetting said internal surface of said shell during or following solidification of said first polymeric solution,
   wherein said electrospun shell comprises a polymer selected from the group consisting of poly (e-caprolactone) (PCL), polyamide, poly(siloxane), poly(silicone), poly(ethylene), poly(vinyl pyrrolidone), poly(2-hydroxy ethylmethacrylate), poly(N-vinyl pyrrolidone), poly(methyl methacrylate), poly(vinyl alcohol), poly (acrylic acid), poly(vinyl acetate), polyacrylamide, poly(ethylene-co-vinyl acetate), poly(methacrylic acid), polylactide, polyglycolide, poly(lactide-coglycolide), polyanhydride, polyorthoester, poly(carbonate), poly(acrylo nitrile), polyaniline, polyvinyl carbazole, polystyrene, poly(vinyl phenol), polyhydroxyacid, poly(caprolactone), polyanhydride, polyhydroxyalkanoate, and polyurethane, and whereas said electrospun coat comprises a polymer selected from the group consisting of poly(acrylic acid), poly (vinyl acetate), polyacrylamide, poly(ethylene-co-vinyl acetate), poly(ethylene glycol), poly(methacrylic acid), polylactide polyglycolide, poly(lactide-coglycolide), polyanhydride, polyorthoester, poly(carbonate), poly (ethylene oxide), polyaniline, polyvinyl carbazole, polystyrene, poly(vinyl phenol), and polyhydroxyacid, and
   wherein said polymer of said first polymeric solution and said polymer of said second polymeric solution are different.

2. The microtube of claim 1, wherein said first solvent of said first polymeric solution evaporates faster than said second solvent of said second polymeric solution.

3. The microtube of claim 1, wherein said second solvent of said second polymeric solution is capable of evaporating through said internal surface of said shell.

4. The microtube of claim 1, wherein a thickness of said shell is from about 100 nm to about 20 micrometer.

5. The microtube of claim 1, wherein an internal diameter of the microtube is from about 50 nm to about 20 micrometer.

6. The microtube of claim 1, wherein said first and said second polymeric solutions are selected from the group consisting of: 10% poly (e-caprolactone) (PCL) in chloroform ($CHCl_3$) and dimethylforamide (DMF) (80:20 by weight) as said first polymeric solution and 4% poly(ethylene oxide) (PEO) in water ($H_2O$) and ethanol (60:40 by weight) as said second polymeric solution, 10% PCL in $CHCl_3$ and DMF (80:20 by weight) as said first polymeric solution and 6% PEO in $H_2O$ and ethanol (60:40 by weight) as said second polymeric solution, 9% PCL in $CHCl_3$ and DMF (90:10 by weight) as said first polymeric solution and 7% PEO in $H_2O$ as said second polymeric solution, 10% PCL in $CHCl_3$ and DMF (80:20 by weight) as said first polymeric solution and 9% poly(vinyl alcohol) (PVA) in water and ethanol (50:50 by weight) as said second polymeric solution, and 10% PCL in $CHCl_3$ and DMF (90:10 by weight) as the first polymeric solution and 4% (by weight) PEO in ethanol:$H_2O$ (26:74 by weight) as a second polymeric solution.

7. The microtube of claim 1, wherein said microtube is filled with a liquid.

8. The microtube of claim 1, wherein said first and said second polymeric solutions are biocompatible.

9. The microtube of claim 1, wherein said cell or said membrane-coated particle-of-interest is attached to said coat over said internal surface of said shell.

10. The microtube of claim 1, wherein said cell or said membrane-coated particle-of-interest is attached to said shell of the microtube.

11. The microtube of claim 1, wherein said shell comprises pores.

12. The microtube of claim 1, wherein said shell prevents diffusion of the cell or the membrane-coated particle-of-interest therethrough.

13. The microtube of claim 1, wherein said cell comprises a prokaryotic cell.

14. The microtube of claim 1, wherein said cell comprises a cell wall.

15. The microtube of claim 1, wherein said polymer comprises a co-polymer.

16. The microtube of claim 1, wherein said polymer comprises a blend of polymers.

* * * * *